(12) United States Patent
Nakajima et al.

(10) Patent No.: US 7,834,065 B2
(45) Date of Patent: Nov. 16, 2010

(54) MEDICAL-USE TWO PART REACTIVE ADHESIVE AND MEDICAL-USE RESIN HAVING SELF-DEGRADATION PROPERTY

(75) Inventors: Naoki Nakajima, Kyoto (JP); Hajime Sugai, Kamigyo-ku (JP); Masakazu Konda, Kyoto (JP); Suong-Hyu Hyon, Sakyo-ku (JP)

(73) Assignee: BMG Incorporated, Kyoto (JP)

( * ) Notice: Subject to any disclaimer, the term of this patent is extended or adjusted under 35 U.S.C. 154(b) by 318 days.

(21) Appl. No.: 11/881,941

(22) Filed: Jul. 30, 2007

(65) Prior Publication Data
US 2008/0319101 A1 Dec. 25, 2008

Related U.S. Application Data

(63) Continuation-in-part of application No. PCT/JP2006/301543, filed on Jan. 31, 2006.

(51) Int. Cl.
*C08L 15/00* (2006.01)
(52) U.S. Cl. ...................................... 523/111
(58) Field of Classification Search .............. 424/70.27, 424/426; 523/111
See application file for complete search history.

(56) References Cited

U.S. PATENT DOCUMENTS

| | | | | |
|---|---|---|---|---|
| 5,900,245 | A * | 5/1999 | Sawhney et al. | 424/426 |
| 5,900,363 | A * | 5/1999 | Hiraki et al. | 435/71.2 |
| 6,165,488 | A | 12/2000 | Tardy et al. | |
| 6,312,725 | B1 * | 11/2001 | Wallace et al. | 424/484 |
| RE38,827 | E * | 10/2005 | Barrows et al. | 514/21 |
| 7,090,846 | B2 * | 8/2006 | Szego | 424/178.1 |
| 2002/0142042 | A1 * | 10/2002 | Mumper et al. | 424/487 |
| 2003/0083286 | A1 * | 5/2003 | Teng et al. | 514/44 |
| 2005/0002893 | A1 * | 1/2005 | Goldmann | 424/70.27 |
| 2005/0069589 | A1 * | 3/2005 | Lowinger et al. | 424/488 |
| 2007/0281904 | A1 * | 12/2007 | Baker et al. | 514/55 |

FOREIGN PATENT DOCUMENTS

| | | |
|---|---|---|
| JP | 9-103479 | 4/1997 |
| JP | 11-239610 | 9/1999 |
| JP | 2004-261590 | 9/2004 |
| JP | 2005-21454 | 1/2005 |
| WO | WO-98/15299 | 4/1998 |

OTHER PUBLICATIONS

1999 "Hemostatic Agent from Modified Gelatin and Polysaccharides" Xiumei Mo et al. Polymer Preprints, Japan vol. 48, No. 3 p. 566.
May 2000 "Soft tissue adhesive composed of modified gelatin and polysaccharides" Xiumei Mo et al. Journal of Biomaterials Science, Polymer Edition vol. 11, No. 4 pp. 341-351.

* cited by examiner

*Primary Examiner*—David Wu
*Assistant Examiner*—Angela C Scott
(74) *Attorney, Agent, or Firm*—Jordan and Hamburg LLP

(57) ABSTRACT

Medical-use two-part adhesive comprising; first part comprised of an aqueous solution or a powder of aldehyde-groups-introduced alpha-glucan; and second part comprised of an aqueous solution or a powder of amino-groups-containing polymer that is formed of a polymer chain of amino-group-containing units and has a molecular weight in a range of 1000 to 20,000; as well as medical-use hydrogel resin obtained by curing the adhesive. A mixture of the first and second parts, at a time of mixing them to form the hydrogel has pH in a range of 5.0 to 8.0. In a preferred embodiment, the amino-groups-containing polymer is epsilon-poly-L-lysine produced by microorganism or by enzyme.

25 Claims, 21 Drawing Sheets

4 day

10/0  8/2  6/4  4/6  2/8  0/10

1 week

10/0  8/2  6/4  4/6  2/8  0/10

2 week

10/0  8/2  6/4  4/6  2/8  0/10

MEDICAL-USE TWO PART REACTIVE ADHESIVE AND MEDICAL-USE RESIN HAVING SELF-DEGRADATION PROPERTY

CROSS-REFERENCE TO RELATED APPLICATIONS

This application is a continuation-in-part (CIP) application of International application PCT/JP2006/301543 (International publication WO/2006/080523), which was filed on Jan. 31, 2006 with claiming priority based on Japan's patent Applications 2005-54577 and 2005-128610 having a filing date of Jan. 31, 2005 and Mar. 29, 2005 respectively; the entire contents of which are incorporated herein by reference.

This application claims a convention priority based on Japan's patent application 2006-323720 that was filed on Nov. 30, 2006.

BACKGROUND OF THE INVENTION

This invention relates to a medical-use adhesive that is used for bonding of living tissues, filling or preventing of adhesion between living tissues, or for stopping of bleeding, after surgical operation or the like, as well as a medical-use resin. Especially, the invention relates to an adhesive that cures after mixing of first and second liquids and then decomposes to be fluidized after elapse of a certain period.

As an adhesive for medical use, especially for surgical operation; (1) cyanoacrylate adhesives and (2) fibrin glue have been predominantly used.

(1) Cyanoacrylate Adhesive

The cyanoacrylate adhesive has been used in industrial use and household use, for original purpose of instantly adhering of; metal, plastics, rubber, wood, ceramics or the like. About ten varieties of the cyanoacrylate adhesive for medical use had been developed by year of 1968. This category of adhesive utilizes that; cyanoacrylate monomers are polymerized and cured in presence of a small amount of water that is a polymerization initiator. And, the polymerization and curing are rapid, and strength of adhesion on living tissues are high. However, cured resin has poor flexibility and is rigid and may thereby deter healing of wounds. Moreover, the cured resin is difficult to be decomposed as to be remained as a foreign body after being enveloped. Further, there has happened to be reported that formaldehyde is produced on way of decomposition of the resin as to exhibit cytotoxicity and/or injuring on tissue.

(2) Fibrin Glue

Fibrinogen forms fibrin masses by action of thrombin; such mechanism of coagulation of blood is utilized in this category of adhesive. The fibrin glue has high compatibility with living body and high convenience in usage and is widely used in arresting of bleeding from a suture part or the like after surgical operation and in enhancing of bonding and closure of tissues. The fibrin glue however has only poor level of adhesive strength so that produced fibrin masses may be occasionally peeled off from the tissue. Moreover, due to being a blood product, there remains a fear of virus transmission.

On the other hand, two-liquid adhesives for surgical use as in (3)-(6) below have been recently proposed.

(3) Dextranaldehyde (oxidized dextran being a polyaldehyde)/high-molecular-weight chitosan—WO 2003/035122 of AESCULAP AG & CO KG (DE); a counterpart of U.S.2005/0002893 A-1 and EP 143 8079 B1.

There has been proposed a two-liquid reaction adhesive for surgical use; a first liquid of which is 15 wt % aqueous solution of dextranaldehyde; and a second liquid of which is 2 wt % or 4 wt % aqueous solution of high-molecular-weight chitosan (Protasan™ UPCL213, FMC Biopolymers). In the adhesive, molar ratio of aldehyde groups to amino groups (aldehyde/amino molar ratio) is "at least three" according to a sole independent claim 1; and curing within 150 seconds was achieved by adopting the aldehyde/amino molar ratios of no less than 6, which are calculated from Table 2 and Table 1. Meanwhile, Table 3 and so on indicate that achieved shear strength was sufficient; and Table 8 indicates that more excellent adhesive strength was achieved by use of high-molecular-weight dextran having an average molecular weight no less than 400,000.

Moreover, last section ("4. Stoppage of Liver Bleeding") of the description indicates that; a two-part reactive adhesive having the aldehyde/amino molar ratio of 13.6 ("DA6" on Table 3), with first liquid to second liquid mixing ratio of 1/1, was effective as haemostatic sealant for rat liver. Curing time of this adhesive was about 15 seconds according to Table 2.

Tables 6 and 7 as well as explanations relevant to these tables indicates that sufficient adhesion strength was achieved even when 20 wt % aqueous solution of polyvinylalcohol-vinylamine graft copolymer (PVALNH$_2$) is used in place of the chitosan aqueous solution. However, molecular weight and composition of the used copolymer were not specified. The curing time was also not specified.

(4) Micelle-forming polymer with aldehyde end groups/high-molecular-weight polyallylamine—JP-2005-021454A; NISHIDA, Hiroshi; YOKOYAMA, Masayuki, "Tissue adhesive formed of polymer micelle as effective component".

JP-2005-021454A discloses two-part reactive "adhesive for animal tissues". Its first liquid is aqueous micelle solution of a polymer having following structure; [end-aldehyde group]-[polyethylene glycol segment having molecular weight of 5500]-[polylactide segment having molecular weight of 4000]. Second liquid of the adhesive is aqueous solution of high-molecular-weight (no less than 60,000) polyallylamine.

It is indicated that; aqueous solution of poly-L-lysine (Table 3 as well as RUN 13-14 and 16 of Table 5) and chitosan aqueous solution (Table 4) may be used as the second liquid, in place of the polyallylamine solution. Paragraph 0031 indicates that oxidized starch and oxidized cellulose may be used for the first liquid. In respect of the poly-L-lysine, RUN 13-14 and 16 of Table 5 indicate that; high molecular weight of 700,000 is needed and a relatively low molecular weight of 30,000 is not adoptable. Moreover, Table 3 as well as RUN 12-16 of Table 5 indicates that; pH of the polylysine aqueous solution as the second liquid has to be no less than 9.0.

(5) Starch aldehyde (oxidized starch being a polyaldehyde)/collagen—WO98/15299; "ADHESIVE COMPOSITION WITH MACROMOLECULAR POLYALDEHYDE BASE AND METHOD FOR CROSS-LINKING COLLAGEN"; a counterpart of Japan's issued patent 323871.

As a first liquid, 0.5 ml of 5 wt % aqueous solution of solubilized starch that has been oxidized to form a polyaldehyde; please see first sentence of Example 3. Molecular weight of the solubilized starch "may be varied in a range of 10,000 to 200,000 dalton" as read from Example 1. While molecular weight of collagen is not mentioned in the specification, the molecular weight is thought to be about 300,000 as in typical collagens. The adhesive is described to be useful in bonding tissues of living body and to have ability for preventing adhesion among tissues. Please see Examples 3-6.

(6) Gelatin/succinimidized poly-L-glutamate—JP-9(1997)-103479 "Medical-use material and its production method".

Aqueous solution containing the gelatin, which is produced by heat-denaturing of collagen, is used as a first liquid; and, an aqueous solution containing succinimidized poly-L-glutamic acid is used as a second liquid; according to a disclosed medical-use adhesive.

Meanwhile, other than the two-part adhesives mentioned above, there have also been proposed medical-use adhesives as in (7)-(8) below.

(7) Gelatin/Dicarboxylic Acid

Gelatin is reacted with dicarboxylic acid as to convert amino groups of the gelatin into carboxylic groups. Such adhesive is disclosed. Please see JP-11 (1999)-239610A ("Medical-use material for bonding tissues of living body as well as production method thereof"). Medical-use adhesives based on the gelatin causes fear of BSE or the like due to use of risk portions of cattle, and hence are avoided to be used in clinical practice.

(8) Urethane Polymer

For example, there is disclosed an adhesive formed of an adduct that is produced by polyol and polyisocyanate. Please see JP2004-261590A ("Medical-use adhesive"). This adhesive has disadvantages in difficulty of handling due to high viscosity and in difficulty of adhesion at portions having lot of blood or body fluid.

BRIEF SUMMARY OF THE INVENTION

Medical-use two-part reactive adhesive of the invention comprises; first part comprising an aqueous solution or a powder of alpha-glucan aldehyde (a polyaldehyde obtained by oxidizing of alpha-glucan) having weight-average molecular weight in a range of 1000 to 200,000; and second part comprising aqueous solution of amino-group-containing polymer formed of chains of amino-group-containing units; wherein weight-average molecular weight of the amino-group-containing polymer is in a range of 1000 to 20,000, and pH of a mixture when the first and second liquid are mixed is in a range of 5.0 to 8.0.

The amino-group-containing polymer is in particular epsilon-poly-L-lysine produced by microorganism or by enzyme.

Preferably, molar ratio of aldehyde groups to amino groups in the mixture of the first and second liquids at a time of mixing them is in a range of 0.2 to 2.0 when the first part is an aqueous solution (first aspect of the invention); and is in a range of 0.2 to 4.0 when the first part is an aqueous solution (second aspect of the invention). Under such molar ratio, hydrogel resin is obtained; and when kept as wet hydrogel, the hydrogel resin changes to sol state by self-disintegration after elapse of a period for keeping hydrogel state, which may be freely set in a range of one day to one month.

When the first part is a powder, application of the adhesive parts may be made as follows; the powder of the first part is applied on a living-body portion to be adhered or treated, on first hand by spraying or the like; and then, the second part as a liquid is applied on the living-body portion. In otherwise, the powder of the first part and the liquid of the second part are mixed with each other; and on right after the mixing, such mixture is applied on the living-body portion. Alternately, when each of the first and second parts is a powder, the powders of the first and second parts may be mixed with each other before the application, as to form a powder mixture adhesive. The powder mixture adhesive may be stored in a bottle and may be applied on the living-body portion, which is wet.

The resin of the invention is a hydrogel resin obtained by mixing the first and second parts of the adhesive; and when kept as fully wet (water-saturated) hydrogel, the hydrogel resin changes to sol state by self-disintegration after elapse of a period for keeping hydrogel state, which may be freely set in a range of one day to one month.

BRIEF DESCRIPTION OF THE SEVERAL VIEWS OF THE DRAWING

FIGS. 2-1 and 2-2 are photographs showing an expansion of cured matter of adhesive that has been applied on a rubber glove (Section 4);

FIGS. 3-1 to 3-3 are photographs showing a time course of disintegration of cured resins of adhesives that have been added with chitosan, up to three weeks after the curing (Section 6);

FIGS. 4-1 to 4-5 are photographs showing a time course of disintegration of cured adhesive being on a liver of domestic rabbit (Section 7);

FIGS. 5-1 to 5-4 are photographs showing a time course of disintegration of cured resins of adhesives, pH of each of which has been adjusted by a mixture of acetic and citric acids (Section 8);

FIGS. 6-1 and 6-2 are electrophoresis patterns of polylysine that has been heat-treated (Section 9);

FIGS. 7-1 to 7-6 are photographs showing a time course of disintegration of the cured resin of adhesive that has been prepared by use of heat-treated polylysine (Section 9);

FIGS. 9-1 to 9-2 are photographs showing a bleeding-arrested state of a rabbit liver by adhesive of the embodiment (Section 13);

FIGS. 10-1 to 10-2 are tissue's sectional images of an affected part 4 weeks after applying the adhesive on a tissue-adhesion-induced area (Section 14);

FIGS. 11-1 to 11-2 are photographs showing that air leakage from an artificially-induced deficient area has been arrested by use of the adhesive of the embodiment (Section 16);

FIGS. 21-1 to 21-3 are a set of photographs indicating a process flow of partially cutting of kidney of a rabbit and arresting of bleeding from cut-out face.

DETAILED DESCRIPTION OF THE INVENTION

Figure 1:
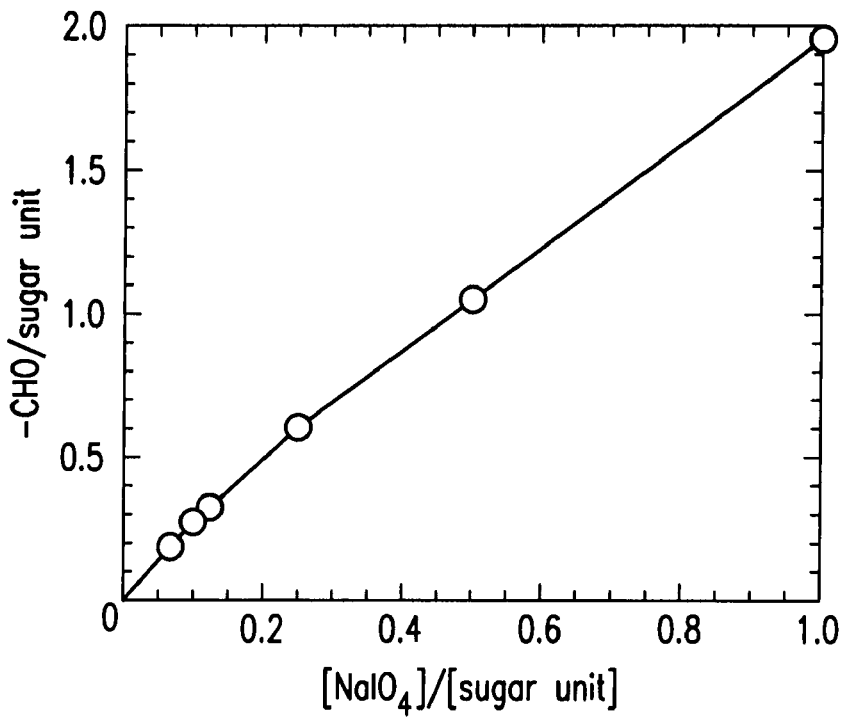
FIG. 1 is a graph showing a relationship between addition amounts of sodium periodate and introduced amount of aldehyde groups (Section 1)

In regard of the fibrin glue, it is not able to induce modification or adjustment of physical property of the cured resin, such as improvement in flexibility in accordance with occasions arisen. Moreover, it is not able to induce prolongation of period, during which the cured resin is degraded in the living body, which lasts typically for one to three days. Meanwhile, cyanoacrylate resin requires a quite a long period for being completely degraded and absorbed in the living body; there is a report saying the period is longer than one year. Thus, designing of the resin as to be completely degraded and absorbed within 1-2 weeks, for example, is not achievable in a practical sense.

For any of the above-mentioned adhesives, the cured resin does not exhibit that degradation or disintegration proceeds rapidly after lapse of a certain period. When period for keeping adhesion strength or the like is taken to be long enough, undesired resin layer or molded resin piece lasts for a considerably long time as to become a problem. Meanwhile, desired length of the period for keeping or timing of starting degradation differs in accordance with categories of diseases and types of surgery. Nevertheless, controlling of the timing of starting degradation in response to detailed requirements has been practically impossible.

When attempt is made to design a resin that rapidly disintegrates after elapse of a designed disintegration period, such designing undergoes considerable constraints as follows. Because of use in the living body, it is required to have high level of safety without cytotoxicity, tissue toxicity and carcinogenicity. Moreover, the adhesive resin have to satisfy properties required for medical-use adhesive in general, such as; (1) excellent adhesion performance on an adherent that is a water-containing or wet living body; (2) relatively rapid curing and setting under normal temperature and normal pressure on surface of tissues of living body; and (3) flexibility at a level not to inhibit physical motion of the adherent while adhering on the adherent such as skins, blood vessels or organs until wound is healed.

Medical-use two-part adhesive of the invention is a two-liquid adhesive in first aspect of the invention; and is a powder-liquid two-part adhesive in second aspect of the invention, in which the first part is a powder. Medical-use two-part adhesive in third aspect of the invention is two-powder adhesive. Concept of powder-liquid two-part adhesive is completely novel and is newly presented, starting from concept of the two-liquid adhesive. The powder-liquid two-part adhesive enables sufficient adhesion even on wet living body portion, to which body fluid such as blood oozes out heavily, and even especially when the wet living body portion is arranged along a vertical plane. Moreover, due to powder form, the alpha-glucan aldehyde as the first part may be preserved in a plastic container under room temperature up to 36 months with causing almost no drop in molecular weight.

The alpha-glucan aldehyde comprising the first part (which is the first liquid in the "first aspect" and is a powder part in the "second aspect") is obtained by oxidizing the alpha-glucan as to introduce aldehyde groups, and has weight-average molecular weight in a range of 1000 to 200,000. The alpha-glucan denotes sugar chains that are formed by alpha linkage of glucoses with each other. Sugar residue of glucan, which is anhydro glucose unit, has a molecular weight of 162.14. The alpha-glucan of the invention includes dextran, dextrin and pullulan, which may be used as mixed with the other. Starch or amylose may be used when properly degraded. Pullulan product of high molecular weight may also be used after being properly degraded. Introduction of the aldehyde groups may be made by typical methods of periodate oxidation. For achieving proper extent of self-degradability, number of the aldehyde groups introduced in one anhydro glucose unit is preferably in a range of 0.1 to 1.0, more preferably 0.2 to 9.0, still more preferably 0.3 to 0.8. For enhancing preservation stability of the first liquid, the preferred number of introduced aldehyde groups to one anhydro glucose unit is relatively low, and as low as 0.2 to 0.4 for example.

Among the alpha-glucan aldehyde, dextran aldehyde and dextrin aldehyde are especially preferred because of stable adhesion performance. Weight-average molecular weight of dextran, which is used in obtaining the dextran aldehyde, is preferably 2000 to 200,000, and more preferably 2000 to 100,000. Adoptable are those commercially supplied by Pharmacosmos A/S for example; and are not only Dextran 40, Dextran 60 and Dextran 70 in medical-use grade but also Dextran T10 to Dextran T2000 among T-Dextran series. Meanwhile, dextrin product commercially supplied by Wako Pure Chemical Industries, Ltd in Japan may be used for example, in obtaining the dextrin aldehyde. Weight-average molecular weight of the dextrin is in a range of 1000 to 10,000 for example. Most preferred molecular weight of alpha-glucan aldehyde varies in accordance with detailed usage; and by selecting ones having certain molecular weight or molecular weight distribution, time length up to fluidization by self-disintegration may be adjusted. When molecular weight of the dextran aldehyde is too large, the fluidization by self-disintegration becomes excessively delayed. Meanwhile, when molecular weight of the dextran aldehyde is too small, time period for keeping the gel state becomes too short.

Weight-average molecular weight and molecular weight distribution of the alpha-glucan may be easily obtained by typical aqueous GPC (gel filtration chromatography, that is, size exclusion chromatography (SEC) in a formal naming) measurement. In detail, GPC columns formed of cross-linked water soluble polymer (TOSOH TSK gel G3000PW and G5000PW, with a TSK guard column PWH) are used as maintained at 40° C., and buffer solution (10 mM $KH_2PO_4$+ 10 mM$K_2HPO_4$) is used as eluent.

Amino-group-containing polymer for forming the second part (which is the second liquid in the "first aspect" and is a liquid part in the "second aspect") is formed of a chain of amino-group-containing units, and has weight-average molecular weight in a range of 1000 to 20,000, preferably in a range of 1000 to 10,000 and more preferably in a range of 1500 to 8000. Preferably, the amino-group-containing polymer does not include high-molecular weight fraction no less than 30,000.

Especially preferred amino-group-containing polymer is substantially consisting of a molecular fraction solely; in a range no less than 1000 and smaller than 30,000, preferably in a range of 1000 to 25,000, and more preferably in a range of 1000 to 20,000, when molecular weight is measured by SDS gel electrophoresis. The "substantially" means that molecular fraction less than 5% in weight ratio or such stain dot pattern should be neglected.

Molecular weight of the polylysine or other amino-group-containing polymer may be obtained with easiness and high accuracy, by any of following methods.

(1) SDS-PAGE (Sodium Dodecyl Sulfate-Polyacrylamide Gel Electrophoresis)

Measurement is easily made by use of an electrophoresis apparatus and a densitograph (AE-6920V), of Atto Corporation in Japan.

(2) Ion Association Chromatography

In ion association chromatography of high-performance liquid chromatography (HPLC), reverse-phase column (TSKgel ODS-80Ts) is used for measurement. In the measurement, acetonitril is used as non-aqueous solvent while applying a gradient; and standard protein marker is used.

(3) Aqueous GPC

Measurement may be made by use of above-mentioned aqueous GPC column for example, which is maintained at 40° C., and by use of an eluent (5% Ammonium Biphosphate/3% Acetonitrile; pH=4.0) that is formed by mixing of GPC-grade distilled water, phosphate buffer and acetonitrile. For obtaining absolute molecular weight, low-angle laser light scattering technique may be used as combined with the GPC technique (GPC-LALLS).

For the amino-group-containing polymer used in the second liquid, preferred is epsilon-poly-L-lysine that is produced by use of microorganism or enzyme and has molecular weight in a range of 1000 to 20,000, especially in a range of 1000 to 6000. Alpha-poly-L-lysine may also be used. Chitosan oligomer or degraded chitosan may also be used when having the proper molecular weight and molecular-weight distribution. Polyglycerin or polyvinyl alcohol having been introduced with amino group side chains might also be used.

In detail, epsilon-poly-L-lysine that is obtained by following may be used, for example. Adopted strain is *Streptomyces albulus* subsp. *Lysinopolymerus* that is shown in Japan's issued patent 3525190 or 3653766. Adopted culture medium is formed of; glucose 5 wt %, yeast extract 0.5 wt %, ammonium sulfate 1 wt %, dipotassium hydrogen phosphate 0.08 wt %, potassium dihydrogen phosphate 0.136 wt %, magnesium sulfate heptahydrate 0.05 wt %, zinc sulfate heptahydrate 0.004 wt %, and ferrous sulfate heptahydrate 0.03 wt %; and is adjusted to pH6.8. After cultivation in this culture medium, the epsilon-poly-L-lysine is separated as collected from the culture medium.

When the polylysine or other amino-group-containing polymer has a too large molecular weight or excessively includes a fraction too large in molecular weight; then time period up to the fluidization by the self-disintegration becomes excessively long.

The amino-group-containing polymer in a certain molecular weight range may be partly replaced with those having higher molecular weight or with those having lower molecular weight. For example, high-molecular-weight chitosan (molecular weight of 200,000 for example) may be added to polylysine solely consisting of molecular-weight fraction in a range of 1000 to 20,000, by up to about 1/1 weight ratio. Amino-group-introduced polyethylene glycol (PEG-NH$_2$), which is formed by introducing amino end groups into polyhydric polyethylene glycol having 2 to 8 hydroxyl groups and having molecular weight of 500 to 1000, may also be added. Preferred ones for such adding is those produced by using sucrose as starting compound as to be highly multifunctional.

Into the second part, acid or acidic salt is added as pH adjuster. Thus, pH of mixture of the first and second liquids at a time just mixed together is adjusted to a value in a range of 5.0 to 8.0, preferably in a range of 5.5 to 7.5, more preferably in a range of 6.5 to 7.5. The second liquid has a pH value preferably in a range of 7.0 to 9.0.

As the pH adjuster, preferably mono- or poly-carboxylic acid or anhydride thereof is added. Examples of preferred carboxylic acids are acetic acid, citric acid, succinic acid, glutaric acid, malic acid, fumaric acid and maleic acid, which are naturally occurred. These carboxylic acids have high pH adjusting ability due to buffering function and are harmless to living body. Inorganic acids or salts such as hydrochloric acid and sulfuric acid may be used alone or combined with the above-mentioned carboxylic acid, so long as the pH is adjusted to a proper value in a range of 5.0 to 8.0. Phosphate buffer solution may also be used.

Selecting either of mono-, di-, and tri-carboxylic acids as the pH adjuster enables controlling of time period up to fluidization of the cured gel, which is occurred by self-disintegration in a state of hydrogel. This is presumably due to a following reason. When polycarboxylic acid is used, quasi-cross linking is occurred between polymer chains of the polylysine or the amino-group-containing polymer, so as to delay the fluidization by the self-disintegration.

In the first aspect of the invention, molar ratio of aldehyde groups to amino groups, at a time the first and second liquids are mixed with each other, is no less than 0.1 and lower than 3, and is preferably in a range of 0.2 to 2.0, more preferably in a range of 0.5 to 1.5. The closer the aldehyde/amino molar ratio becomes to 1, the smaller the residue aldehyde groups or the residue amino groups becomes. Thus, this is meaningful in further decreasing toxicity. Concentration of the alpha-glucan aldehyde in the first liquid is typically in a range of 5 to 50 wt %, and preferably in a range of 15 to 25 wt %. Concentration of the amino-groups-containing polymer in the second liquid is typically in a range of 0.5 to 60 wt %, preferably in a range of 5 to 50 wt % and more preferably in a range of 5 to 20 wt %. Too low level of the concentration in the first or second liquid causes problems such as insufficient curing reaction; and too high level of the concentration induces high viscosity of the adhesive liquid as to make it difficult to be handled.

In the second aspect of the invention, molar ratio of aldehyde groups to amino groups, at a time powder-form first part and liquid-form second part are mixed with each other, is no less than 0.1 and lower than 5, and is preferably in a range of 0.2 to 4.0, more preferably in a range of 1.0 to 3.5. In each aspect of the invention, when the aldehyde/amino molar ratio underruns the corresponding range, the disintegration of the hydrogel becomes too rapid; and when the aldehyde/amino molar ratio exceeds the corresponding range, prompt gelation or curing is not achievable. As for a powder of alpha-glucan aldehyde as the first part of the adhesive, anyone may be used as far as being excellent in dispersion and dissolving ability. As for shaping of the powder, anyone may be adopted as far as the particle size is no more than 1 mm and the powder is easily sprayed.

In third aspect of the invention, each of the first and second parts of the two-part adhesive is a powder; and such powder-form first and second parts may be sprayed with a jet of compressed air or the like, as to be applied, in same manner with applying the powder-form second part of the adhesive in the second aspect. The powder-form first or second part may be sprayed to be applied directly on a wet body portion that is wet or soaked with blood, body fluid or the like. Application procedure by way of spraying or the like is preferably made twice or more as to be repeated, in view of achieving evenness of the application. At an interval between such repeated application procedures, and at completion of such application procedures, physiological saline or distilled water is dropped or sprayed on the body portion to be adhered or treated. Such dropping or spraying may be made by dropping with a small syringe having a syringe needle of small diameter, or by a finger-pump spray bottle. When the living body portion or affected area to be adhered or treated is not full of moisture, it is preferred to spray there the physiological saline or the like on beforehand of first application of mixture of the powder-form first and second parts.

The powder-form first and second parts of the adhesive may be successively applied onto the living body portion. Nevertheless, it is preferable to mix on beforehand the first and second parts having a ratio of aldehyde groups to amino groups at around 1/1 as to prepare a powder mixture adhesive, which is to be applied on the living body portion. Adopting of such powder mixture adhesive facilitates; procedures for applying the adhesive and curbing portion-wise variations of mixing ratio; and is thus preferred to achieve reliable adhesion. The powder mixture adhesive may be preserved for a long time under room temperature, in an air-tightly sealed bottle or in a bottle having desiccant for dehydration. Meanwhile, instead of spraying with compressed air or gas, the powder mixture adhesive may be instantly dispersed in water and be sprayed with compressed water.

The first and second parts of the adhesive may be easily sterilized by irradiation with radioactive rays, preferably by irradiation with 10 to 50 Kgy of electron beams and more preferably by irradiation with 20 to 30 Kgy of electron beams. Conditions of the irradiation sterilization are set in a manner that no adverse effect is incurred on performance of the adhesive such as cure time.

Mixing of the first and second parts and application may be in various ways when to use the two-part reactive adhesive of the invention. For example, either of the first and second parts is applied, as it is, on surface of the adherent, and subsequently another of the first and second parts is applied on the adherent as to achieve the mixing. Alternatively, the first and second parts as liquids are mixed in a mixing cavity within an application device and thereafter emitted from spray nozzle as to be applied as sprayed. For some instance, the adhesive may be used, other than in bonding, to obtain a gel resin in a sheet form or the like that is used to prevent adhesion between the tissues. Mixing ratio of the first liquid to the second liquid by volume is typically in a range of 0.5 to 2.0, preferably is set to be about 1.0, which means mixing with almost equal amounts.

When the first and second parts are mixed with each other, aldehyde groups on the alpha-glucan aldehyde are reacted with amino groups on the amino-groups-containing polymer as to form Schiff linkages, which makes cross linkages so as to form hydrogel having network structure of the polymer chains. Resultantly, curing is made within 2 to 150 seconds, preferably within 3 to 100 seconds, and more preferably within 5 to 50 seconds, from the mixing. Preferred time period up to the curing from the mixing varies to a certain extent in accordance with usages, and is no less than 10 seconds, no less than 15 seconds in particular, when to penetrate into inside of living tissues to exhibit high level of adhesion strength.

Cured adhesive layer or resin in a state of hydrogel, which is formed by curing reaction, changes into fluid state by self-disintegration when a designed fluidization period has elapsed. In other words, the cured adhesive layer or the resin, if being kept as a hydrogel, changes into a fluidized state, which is a flowable sol state, even without undergoing enzymatic degradation. Therefore, the cured adhesive layer or the resin, when being placed in living body, disappears after elapse of a predetermined time period, by being absorbed or excreted. The designed disintegration time period may be arbitrarily set in a rage of a few hours to 4 months, typically in a range of one day to one month, especially in a range of two days to two weeks.

On contrary, conventional biodegradable resins, which are degraded and absorbed in living body only through enzymatic degradation, vary in respect of time period for the degradation. It has been difficult to design the conventional biodegradable resins so as to be rapidly degraded after elapse of a required time period for keeping the adhesion strength.

The time period for self-disintegration may be arbitrarily controlled and set; by selection or controlling of molecular weights of, and molecular-weight distribution, of the alpha-glucan aldehyde and/or the amino-group-containing polymer; by use or non-use and selection of polycarboxylic acids; and by controlling of pH at a time the first and second liquids are mixed. Thus, it is able to arbitrarily design the time period for being disintegrated and absorbed, by controlling of compositions of the two-part adhesive.

While mechanism of the self-disintegration is not clear, we consider that; alpha-glucoside linkage adjacent to the Schiff linkage has become easy to be cleaved where aldehyde groups of the alpha-glucan aldehyde have reacted with the amino groups.

Adhesives utilizing the Schiff base forming reaction have been conventionally used. Nevertheless, no adhesives having self-degradation property have been developed. Reason for this is presumably that; high-molecular-weight polymers have been used as the aldehyde-groups-containing polymer and as the amino-groups-containing polymer. In particular, as the amino-groups-containing polymers, ones having molecular weight no less than several dozen thousands have been used without exception. Because the amino-groups-containing polymer would not degrade, using of high-molecular-weight ones thereof leads to that; no disintegration of the cured resin occurs even when the alpha-aldehyde dextran is degraded. Meanwhile, even when molecular weight of the amino-groups-containing polymer is small, using of high-molecular-weight ones of the aldehyde-groups-containing polymer leads to that; cured resin would not be self-disintegrated within a month.

Conventionally, there has been presumably prevailed a prejudice that; high-molecular ones of the aldehyde-groups-containing polymer has to be used when for achieving the adhesion performance.

The medical-use adhesive and medical-use resin of the invention may be preferably applied for bonding in the living body, filling between tissues, haemostasis, embolization of vessels, sealing of aneurysm, and substrate for drug delivery system (DDS).

EMBODIMENTS OF THE FIRST ASPECT

Two-Liquid Medical Adhesive

1. Controlling of Amount of Introducing Aldehyde Groups by Sodium Periodate.

Five grams of dextran (Wako Pure Chemical Industries, Ltd; Lot No. EWN0778) having weight-average molecular weight of 200,000 was dissolved in 100 ml of distilled water. Then, various amount of sodium periodate (MW 213.89) was added and stirred at 40° C. for 5 hours as to proceed reaction. After the reaction, solution was subjected to dialysis for 24 hours by use of distilled water and dialysis membrane of fractioning molecular weight of 14,000, and thereafter being freeze dried. Thus, the dextran aldehyde was obtained.

In respect of each dextran aldehyde product, amount of introduced aldehyde groups was measured. Obtained is a relationship between; molar amounts of the added sodium periodate and molar amounts of the introduced aldehyde groups, with respect to each anhydro glucose unit of dextran. Result is shown in FIG. 1.

The amount of the introduced aldehyde groups was measured by redox titration method. In detail, 20 mL of 0.05 mol/L iodine aqueous solution, 10 mL of 10 mg/mL dextran aldehyde solution and 20 mL of 1 mol/L sodium hydroxide aqueous solution were charged into a 100 mL Erlenmeyer flask, and stirred at 25° C. for 15 minutes. Then, the solution was added with 15 ml of 6 v/v % sulfuric acid aqueous solution, and was titrated with 0.1 mol/L sodium thiosulfate aqueous solution. Time point at which reaction system becomes colorless and transparent was deemed as ending point, while starch aqueous solution was used as indicator.

As shown in FIG. 1, the amount of the introduced aldehyde groups increases linearly with increase of amount of the added sodium periodate. When the molar amount of the added sodium periodate per anhydro glucose unit is in a range of 0.05 to 1.0, the amount of the introduced aldehyde groups per anhydro glucose unit is in a range of 0.1 to 2. Thus, when one mole of sodium periodate is added with respect to one mole of anhydro glucose unit, two aldehyde groups are introduced to each anhydro glucose unit on average. Thus, it was revealed that efficient oxidation is achieved.

2. Measurement of Cure Time

Twenty grams of dextran (Wako Pure Chemical Industries, Ltd; Lot No. EWR5671) having weight-average molecular weight of 40,000 was dissolved in 100 mL of distilled water. Then, 10 g or 5 g of sodium periodate was added and stirred at 50° C. for 3 hours as to proceed reaction. After the reaction, obtained solution was subjected to dialysis for 24 hours by use of distilled water and dialysis membrane of fractioning molecular weight of 14,000, and thereafter being freeze dried. Thus, the dextran aldehyde was obtained. Each of dextran aldehydes was dissolved in distilled water to prepare 20 wt % solution and was used as the first liquid of the two-liquid reactive adhesive.

Then, 25 wt % epsilon-polylysine aqueous solution (molecular weight of 4000; Chisso Corporation, Lot No. 2050506, free amine) was added by 1 mL of acetic acid and 1.5 mL of distilled water as to prepare 20 wt % polylysine neutral aqueous solution. Meanwhile, polyethylene glycol amine having an amino group on each of two ends (two-functional PEG-$NH_2$, free amine) and having molecular weight of 3000 was dissolved in distilled water as to prepare 30 wt % and 50 wt % aqueous solutions (free amine). Further, polyethylene glycol having an amino group on each end of four branches and having molecular weight of 5000 (four-functional PEG-$NH_2$, free amine) was dissolved in distilled water to prepare 50 wt % aqueous solution. Each of these aqueous solutions of amino compounds was used as the second liquid of the two-liquid reactive adhesive.

Subsequently, 0.5 mL of the second liquid of the two-part reactive adhesive was taken into glass test tube having diameter of 16 mm, into which magnetic stirrer bar having a diameter of 4 mm and a length of 10 mm was putted, and was heated to 37° C. and stirred at a rate of 100 rpm. And, 0.5 mL of the second liquid of the second liquid, which had been preheated to 37° C., was added to the solution by micropipette. Time length up to a timepoint at which the stirrer bar ceased its rotating as a result of curing was measured by use of a stopwatch. Table 1 shows results for the adhesive having the first liquid that is prepared by "10 g addition" of sodium periodate; and table 2 shows that results for the adhesive having the first liquid that is prepared by "5 g addition". In the tables 1 and 2, only those adopting the 20 wt % neutral polylysine aqueous solution as the second liquid are Examples (Example 1 and Example 2 in the tables 1 and 2 respectively) of the invention. When solutions of the polyethylene glycol having amino end groups are used, strength of the gel adhesive layer was insufficient and the self-disintegration within time period of 1 day to 1-2 months was not achieved.

TABLE 1

10 g $NaIO_4$ addition on obtaining the first part
(10 g $NaIO_4$/20 g Dextran 40K, 20 wt % aq. soln.)

| Amino compound | Concentration (%) | Liquid property | Cure time (second) |
| --- | --- | --- | --- |
| Polylysine | 25 | Basic | <1 |
| 20 wt % polylysine with 2% acetic acid | 20 | Neutral | 4.55 ± 0.12 |
| Two-functional PEG-$NH_2$ | 50 | Basic | 10.51 ± 0.19 |
| Two-functional PEG-$NH_2$ | 30 | Basic | 16.35 ± 0.58 |
| Four-functional PEG-$NH_2$ | 50 | Basic | 6.30 ± 0.21 |

TABLE 2

5 g $NaIO_4$ addition on obtaining the first part
(5 g $NaIO_4$/20 g Dextran 40K, 20 wt % aq. soln.)

| Amino compound | Concentration (%) | Liquid property | Cure time (second) |
| --- | --- | --- | --- |
| Polylysine | 25 | Basic | 1.31 ± 0.04 |
| 20 wt % polylysine with 2% acetic acid | 20 | Neutral | 10.57 ± 0.03 |
| Two-functional PEG-$NH_2$ | 50 | Basic | 23.38 ± 2.59 |
| Two-functional PEG-$NH_2$ | 30 | Basic | 33.92 ± 0.34 |
| Four-functional PEG-$NH_2$ | 50 | Basic | 18.51 ± 0.31 |

As shown in Tables 1 and 2, gelling time of an adhesive formed of the four functional PEG-$NH_2$ as amino compound is shorter than that formed of two functional PEG-$NH_2$, which has smaller number of functionality. An adhesive formed of the polylysine, which has one amino group on every anhydro glucose unit on average, has the gelling time shorter than those on above. The larger the concentration of the amino compounds, the more rapid becomes the curing. The gelling time for adhesives of "10 g $NaIO_4$ addition" tends to become about half of that for adhesives of "5 g $NaIO_4$ addition". These results reveal that the curing time may be controlled by number of the aldehyde groups and categories and concentration of the amino compound.

3. Cytotoxicity Test

Twenty grams of dextran (Wako Pure Chemical Industries, Ltd; Lot No. EWK3037) having weight-average molecular weight of 75,000 was reacted with 5 g of sodium periodate, and the dextran aldehyde was obtained in accordance with methods in Section 2. Then, 20 wt % aqueous solution was prepared as the first liquid.

Meanwhile, 10 mL of 25 wt % polylysine aqueous solution that was used in Section 2 was added with 0.5 g of succinic anhydride and 14.5 mL of distilled water as to prepare 10 wt % neutral polylysine aqueous solution, which was used as the second liquid (Reference Example 3). Meanwhile, about 0.5 g of 30 wt % formaldehyde aqueous solution and 0.5 g of 25 wt % glutaraldehyde aqueous solution were precisely weighed, and respectively used for preparing 25 mL of aqueous solutions. By use of each of thus obtained aqueous solutions, cytotoxicity test was conducted in accordance with as follows.

The cytotoxicity test was made according to methods described in J. Biomed. Mater. Res. 29, 829-835 (1995) and by use of a mouse established cell line L929. In detail, cell dispersion was prepared to be 10,000 cells/mL; and 0.1 mL of the cell dispersion was sowed in each well of the 96-well culture plate and incubated at 37° C. for 3 days. Subsequently, each of the aqueous solutions mentioned above was diluted to one of various concentrations, and was charged into respective well by 0.1 mL. Then, incubation was further continued for 2 days. Subsequently, 0.1 mL of neural red culture-medium solution as prepared as 150 microgram/mL was added into the each well; and the incubation was made at 37° C. for 3 hours. After the incubation, culture medium was removed; and the cells were fixed by 1 wt % glutaraldehyde aqueous solution and thereafter air-dried. Subsequently, 0.1 mL of water/ethanol solution (equal-volume mixture) having 1 wt % of acetic acid was added; and then neural red molecules that had been taken into the cells were extracted. Light absorbency at 541 nm was measured and NR50 values were obtained from result of this measurement. The NR50 value indicates a concentration at which 50% of the cells are killed. The smaller the NR50 value becomes, the larger becomes the toxicity.

Table 3 shows the NR50 values of various compounds.

TABLE 3

Cytotoxicity Evaluation Results

| Sample | Component | NR50 value (μg/mL) |
| --- | --- | --- |
| First liquid | Dextran aldehyde | 6,019 ± 91 |
| Second liquid | Polylysine | >10,000 |
| | Formaldehyde | 1.7 ± 02 |
| | Glutaraldehyde | 3.9 ± 0.7 |

As shown in the table, the NR50 value of the dextran aldehyde was larger than 6000 μg/mL and was less than 1/3500 of that of the formaldehyde and less than 1/1500 of that of glutaraldehyde. It was revealed that toxicity of the dextran aldehyde is trifle, even though the dextran aldehyde is also an aldehyde compound. Meanwhile, toxicity of the polylysine was revealed to be extremely low; and it is considered that each component of the adhesive has extremely high safety.

4. Evaluation of Flexibility of the Cured Resin by Use of a Rubber Glove

Figures 1, 2:
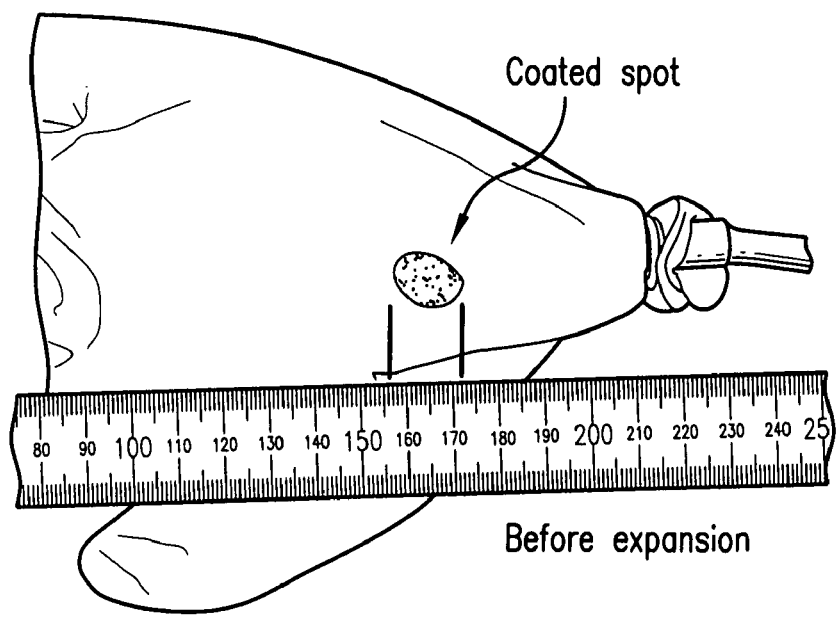
Figure 2:
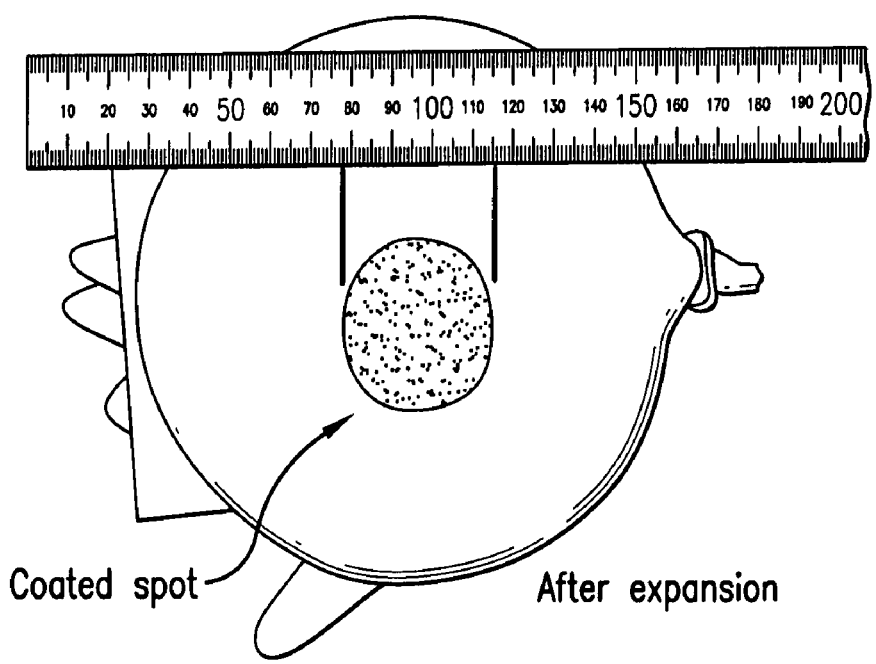

As the first and second liquids, adopted respectively were the 20 wt % aqueous solution of the dextran aldehyde (20 g of dextran is reacted with 10 g of sodium periodate) and 20 wt % neutral polylysine aqueous solution, which are obtained in Section 2. In other words, two-part adhesives of the Examples 1 and 2 were used. The first and second liquids, as are, were mixed together by a mixing device dedicated solely for such adhesives and then applied on a rubber glove for laboratory, by 0.5 mL (0.25+0.25 mL), as to be thinly spread. The adhesive layer was left standstill for about one minute as to achieve curing of the adhesive. Air is pumped into the rubber glove by use of air pump as to make expanding of the cured adhesive layer. FIGS. 2-1 and 2-2 show respectively states of the cured adhesive before the expanding (2-1) and after the expanding (2-2). In the figures, what is stained with Blue No. 1 (Wako Pure Chemical Industries, Lot No. KLN3789) is a gel of the cured adhesive.

As shown in FIGS. 2-1 and 2-2, the cured adhesive was enlarged by three times in diameter by pumping of the air, and then neither crack nor fracture was observed. This result reveals that the adhesive of this example (Example 1) is extremely pliable even after the curing. A gel resin layer having similar flexibility and toughness was also obtained; when molecular weight of dextran is varied to 40000, when addition amount of the sodium periodate per 20 g of dextran is varied to 3 g or 5 g or the like, and when dextrin is used; though photos and data are omitted here.

5. Evaluation of Adhesion Strength by Use of Rabbit Leather

The 20 wt % dextran aldehyde aqueous solution obtained at Section 4 was used as the first liquid. Adopted as the second liquid were; the 20 wt % neutral polylysine aqueous solution, 30 wt % and 50 wt % two-functional PEG-NH$_2$ aqueous solutions, and 50 wt % four-functional PEG-NH$_2$ aqueous solution. Only the adhesive adopting the 20 wt % neutral polylysine aqueous solution as the second liquid is of an example (Example 1) of the invention.

Defatted leathers (1×6 cm) from back skin of domestic rabbit were prepared, on surfaces of which about 10 μL of the first liquid and about 10 μL of the second liquid are successively applied on an area of 1×1 cm. After sufficient mixing, the defatted skin, which had same size and not been applied with the adhesive, was overlaid as to stick onto the one having been applied with the adhesive. Then, such stuck pair of the leathers was applied with 200 g of load and was left as it is for 5 minutes. Then, the stuck pair of the leathers was immediately subjected to a peel test by a tensile testing machine ("Autograph AGS-5KNG", SHIMADZU RIKA CORPORATION) so that shear strength was applied by pulling at a rate of 10 mm/min until the stuck pairs of skins were peeled apart. Load at a time of the peeling apart was taken as adhesion strength. For comparison, fibrin glue ("Bolheal", KAKETSUKEN in Japan) was tested in same manner with above. Table 4 shows these results.

TABLE 4

Adhesion strength evaluation by use of rabbit leather

| Sample | | Adhesion strength |
| --- | --- | --- |
| First liquid | Second liquid | (g/cm$^2$) |
| Dextran Aldehyde (5 g NaIO$_4$/20 g Dextran 40K, 20 wt %) | Polylysine | 144.8 ± 7.6 |
| | Two-functional PEG-NH$_2$, 30 wt % | 10.6 ± 0.8 |
| | Two-functional PEG-NH$_2$, 50 wt % | 14.9 ± 0.7 |
| | Four-functional PEG-NH$_2$, 50 wt % | 160.5 ± 0.9 |
| Fibrin glue | | 28.7 ± 1.3 |

As shown in Table 4, the adhesives respectively adopting the polylysine aqueous solution and the four-functional PEG-NH$_2$ aqueous solution have adhesion strengths far higher than that of the conventional adhesive of fibrin glue.

6. Disintegration Controlling of the Cured Resin by Chitosan Addition

The 20 wt % dextran aldehyde aqueous solution obtained at Section 4 was used as the first liquid. Meanwhile, chitosan product of YAEGAKI Bio-industry, Inc., which has molecular weight of 100,000 and deacetylation degree of 80%, was dissolved in 5 wt % acetic acid aqueous solution, as to prepare 5 wt % chitosan solution. The 5 wt % chitosan solution was mixed with the 20 wt % neutral polylysine aqueous solution obtained in Section 4, in various volume ratios; and such mixtures were used as the second liquid. In other words, the adhesive of the Example 1 was modified such that the second liquid was partially replaced with the chitosan solution.

Figures 1, 3:
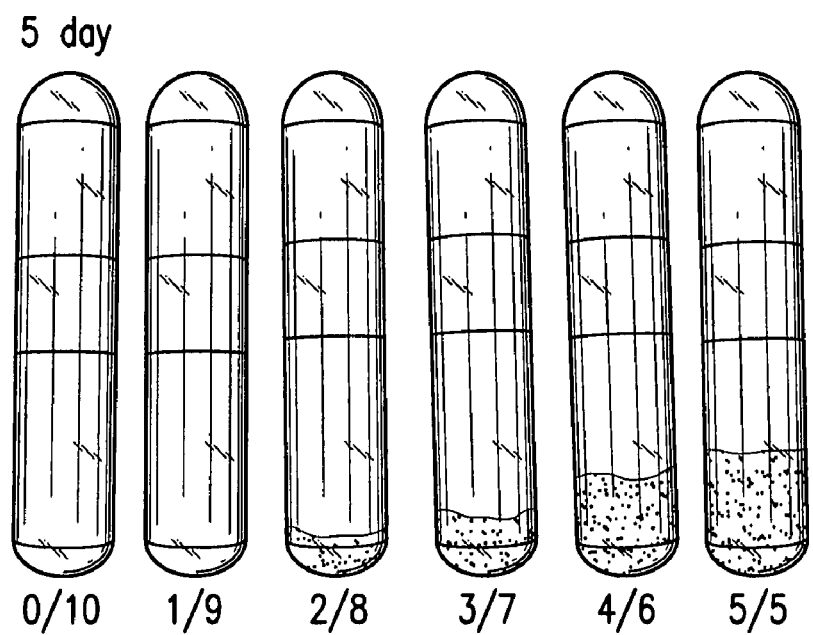
Figures 2, 3:
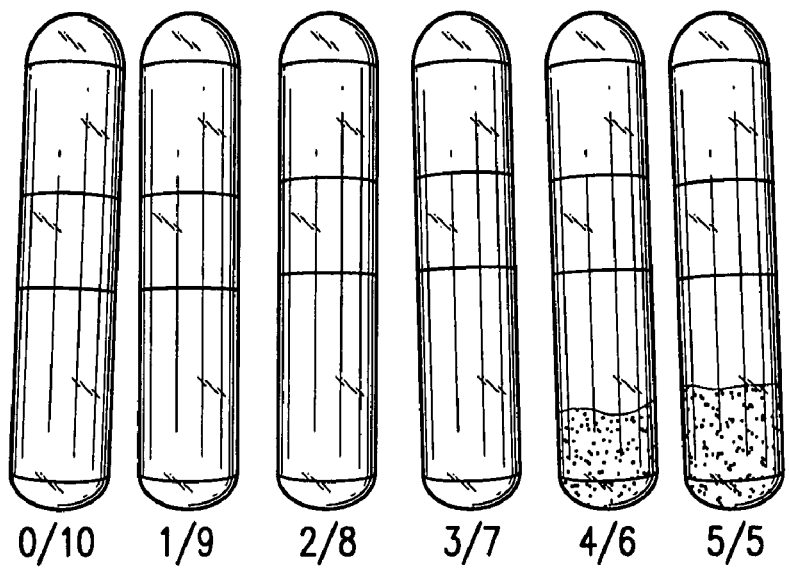
Figure 3:
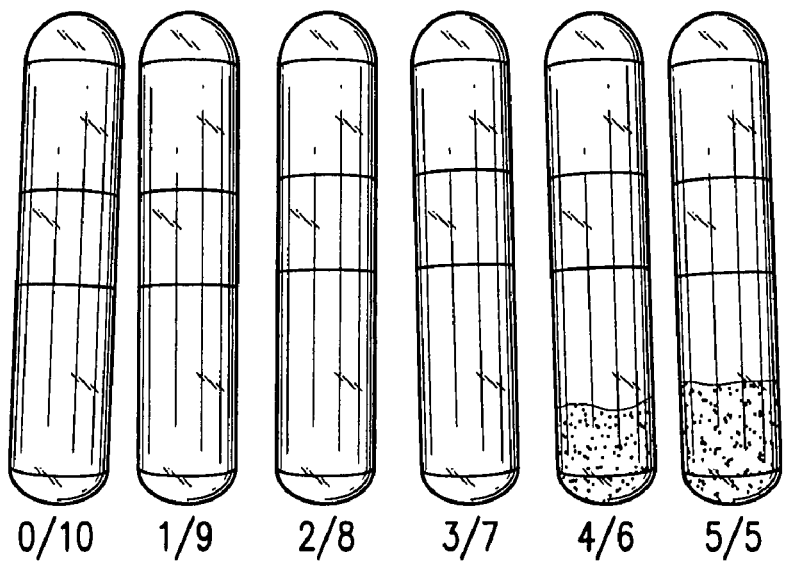

Subsequently, into a 16 mm-diameter glass test tube, each of the first and second liquids was charged as it was (without dilution or addition), by 1 mL. After curing of the liquids, 3 mL of phosphate buffer solution was added into each of the test tubes; and thereafter the test tubes were air-tightly sealed. Then, the test tubes were put into a dryer of 37° C., and disintegration of the adhesives was observed in a time course. FIG. 3 shows states of the adhesives after elapse of 5 days after the curing. On FIG. 3, denotation under each of the test tubes designates volume ratio between the 5 wt % chitosan solution and the 20 wt % neutral polylysine aqueous solution.

As shown in FIG. 3, the adhesives of the embodiments having small chitosan contents (volume ratio 0/10 and 1/9) completely disintegrated within 5 days. Increase of the chitosan content resulted in increase of remaining amount of the cured resin; and the adhesive of 5/5 volume ratio did not show disintegration even after elapse of 3 weeks. These results reveal that time-wise ratio of the disintegration or time period up to the fluidization of hydrogel resin is able to be controlled by specie of the amino compounds and mixture ratios.

As seen from these results, when the solution of chitosan having relatively small value of 100,000 was solely used as the second liquid of the two-liquid reactive adhesive, the self-disintegration property of the invention was never observed. This fact indicates that no advantageous effect of the invention would be obtained, even when linear polymer of amino-group-containing units is used, unless; the polymer has molecular weight of no more than dozen thousands, especially no more than 20,000.

7. In Vivo Disintegration Rate Evaluation of the Cured Adhesive

As the first liquid, the 20 wt % aqueous solution of dextran aldehyde having molecular weight of 75,000 used in Section 3 was adopted. The 10 wt % neutral polylysine aqueous solution same as in Section 3 was prepared and used as the second liquid. Consequently, the adhesive of the Example 1 was adopted. For evaluating time-wise rate of in vivo disintegration of the cured adhesive, following test was made by use of female domestic rabbit having weight of 2.5-3.0 kg.

Nembutal was injected through an ear vein by amount of 0.6 mL per kilogram of body weight, and then Selactar was injected through leg muscle by amount of 0.1 mL per kilogram of body weight, as to achieve anesthesia. After opening of abdominal cavity, a filter paper (TOYO Roshi No. 2) having a cut-out opening at a diameter of 10 mm was pasted on a liver surface. Then, the first and second liquids were mixed with each other by use of a mixer device dedicated to such mixing; and 1 mL of mixed liquid was applied on the liver surface. After the curing, the abdominal cavity was closed, and a time course of the disintegration of the cured resin was investigated.

Figures 1, 4:
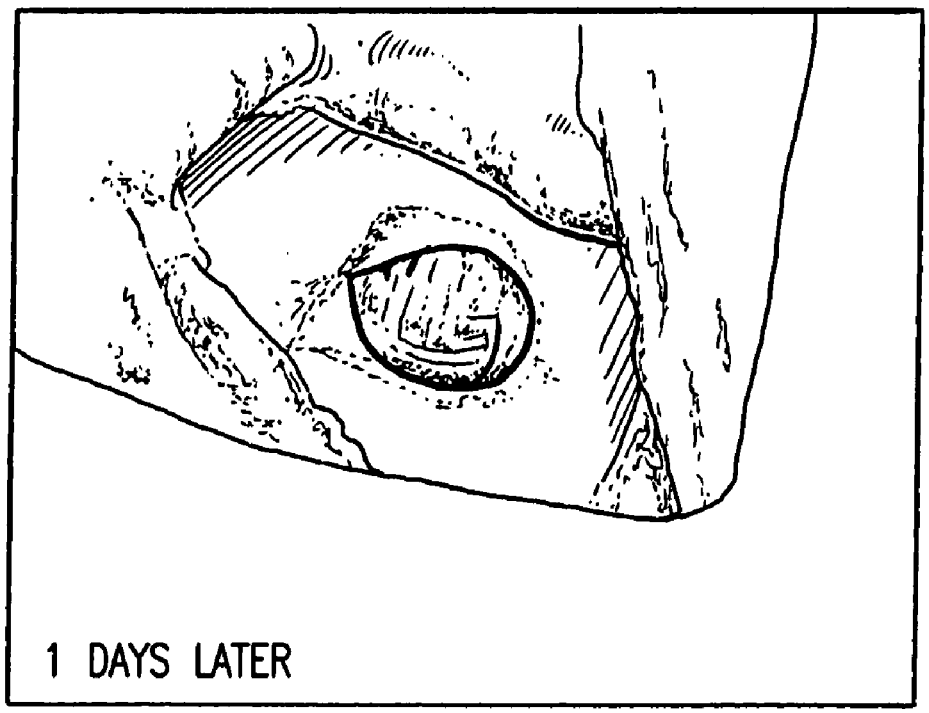
Figures 2, 4:
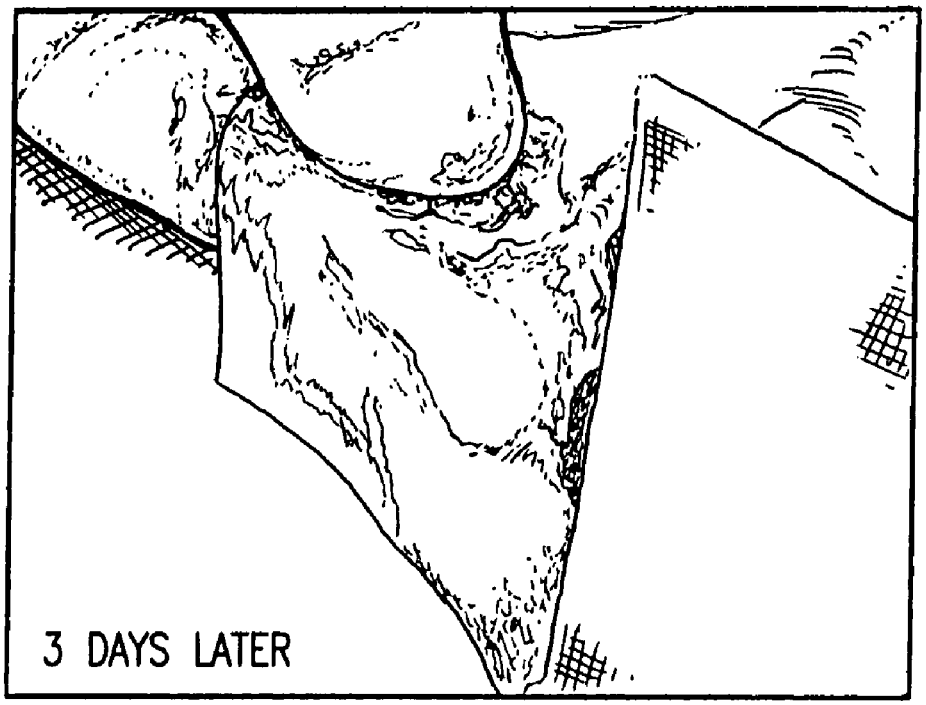
Figures 3, 4:
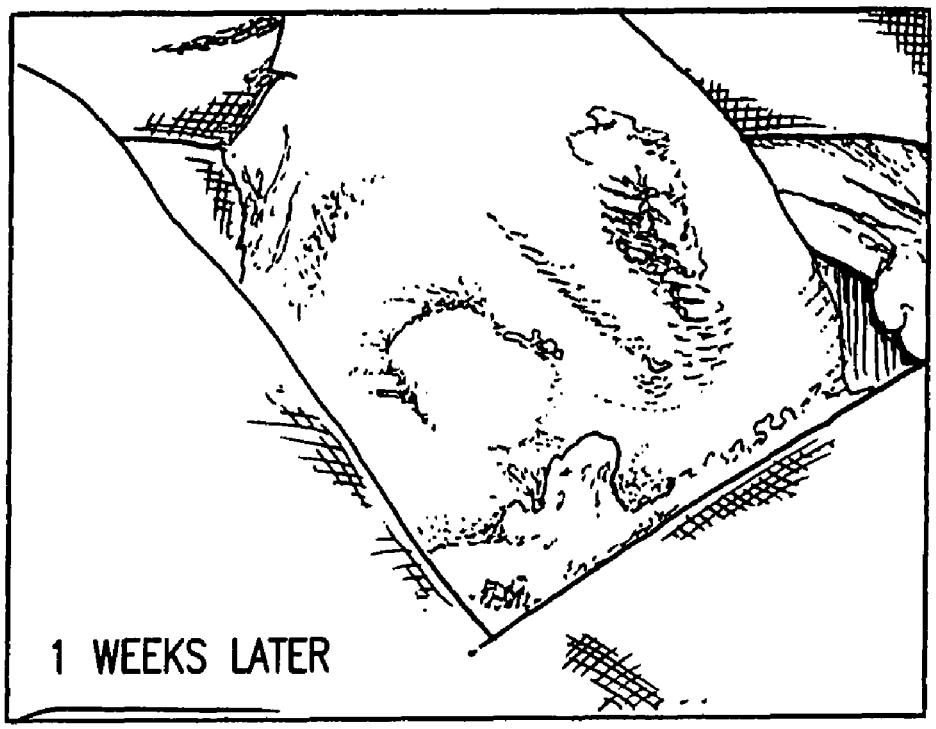
Figure 4:
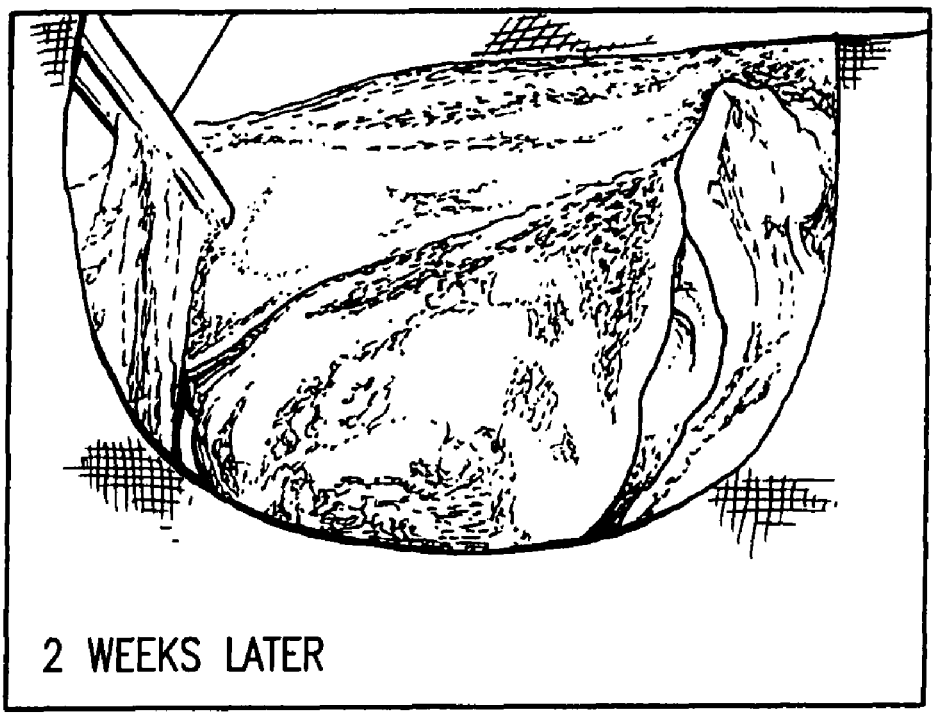

FIGS. 4-1 to 4-3 show disintegration of the cured adhesive. It was determined that the disintegration gradually starts at elapse of 3 days after implanting of the adhesive and that about 90% of the cured adhesive had been disintegrated at an elapse of 4 weeks. Neither tissue reaction nor adverse effect that would be feared especially from image of tissue section was observed, as to show high safety of the adhesive. On course of the disintegration test, there was observed neither decrease of appetite of the rabbit nor other adverse effect due to implanting of the adhesive.

8. Controlling of Disintegration of the Cured Adhesive by Addition of Citric Acid The 20 wt % dextran aldehyde aqueous solution obtained in Section 4 was used as the first liquid. Meanwhile, 10 mL of the 25 wt % polylysine aqueous solution having basicity used in Section 2 was added with acetic acid and citric acid, by combined amount of 1 mL, with various ratios between the acids; and further added with 0.5 mL of distilled water as to form a 20 wt % neutral polylysine aqueous solution, which was used as the second liquid. In other words, the two-part adhesive of the Example 1 and the two-part adhesive of the Reference Example 3 (Section 3) were mixed in ratios of 8/2, 6/4, 4/6 and 2/8, as to prepare adhesives of embodiments of the invention. The adhesive same as the Example 1 solely using acetic acid (10/0) for neutralization, as well as the adhesive same as the Reference Example 3 solely using citric acid (0/10), are prepared and used for comparison.

Figures 4, 5:
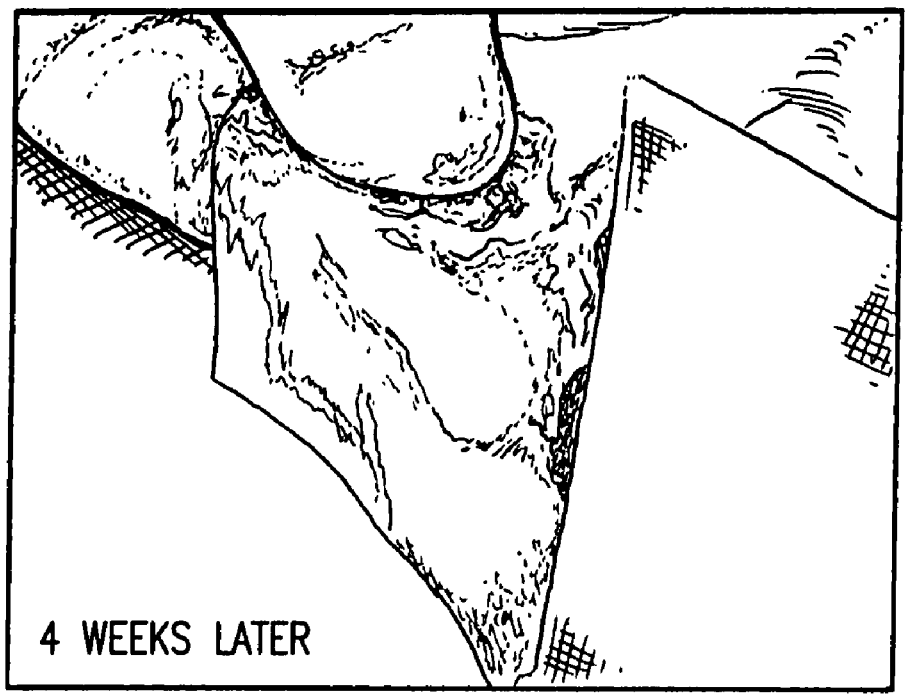
Figures 1, 5:
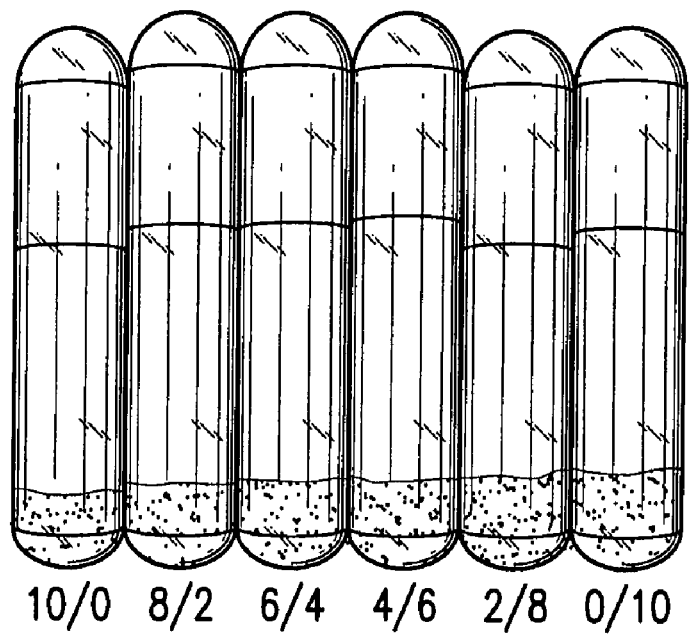
Figures 2, 5:
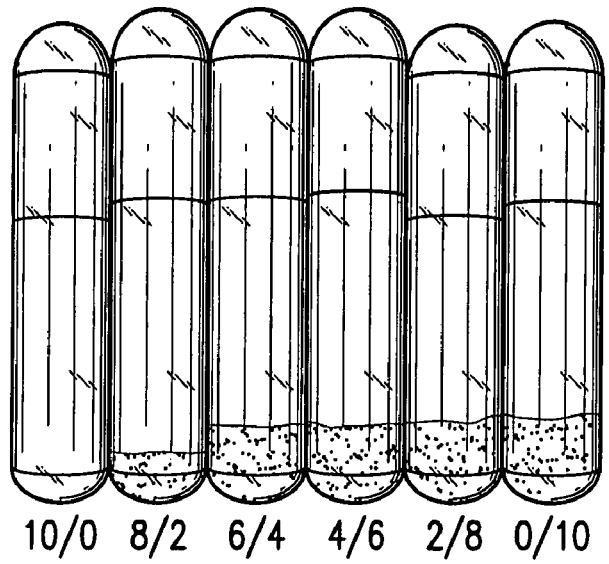
Figures 3, 5:
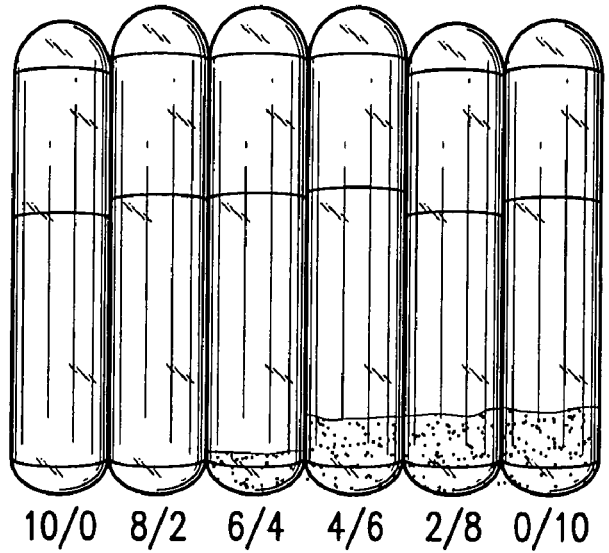
Figures 4, 5:
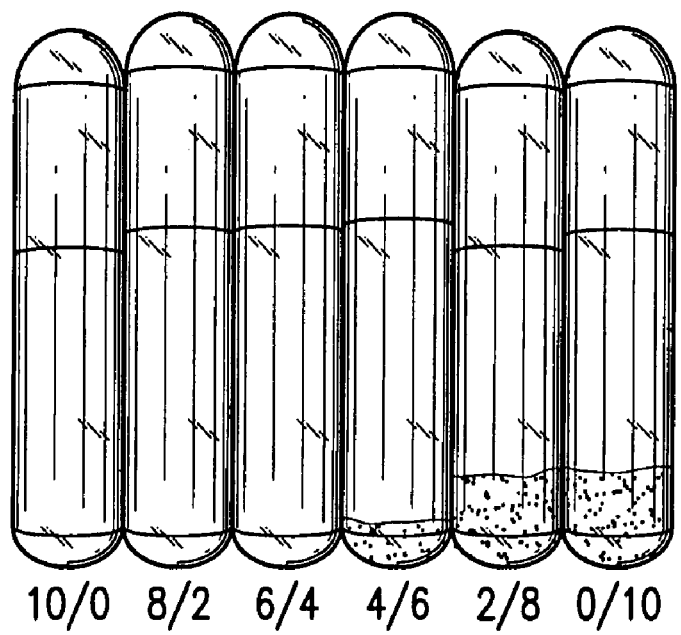

Subsequently, disintegration rate of the cured adhesive was evaluated by a method described in Section 6. Results of the evaluation are shown in FIG. 5. Denotations in the figure indicates weight ratios between acetic acid and citric acid; and as for left-end one, pH adjustment is made solely by acetic acid, while solely by citric acid as for right-end one. When acetic acid was solely used for pH adjustment of the polylysine aqueous solution, the cured adhesive completely disintegrated at elapse of 4 days. The disintegration was delayed by increase of citric acid. When citric acid was solely used for pH adjustment of the polylysine aqueous solution, the cured adhesive kept its original shape even at elapse of 2 weeks and required no less than 2 months for complete disintegration. These results indicate that disintegration rate is easily controlled by selecting species and amount of pH adjuster.

9. Conversion of Polylysine to High-Molecular-Weight One by Heating and its Effect on Disintegration Rate of the Cured Resin.

Figures 1, 6:
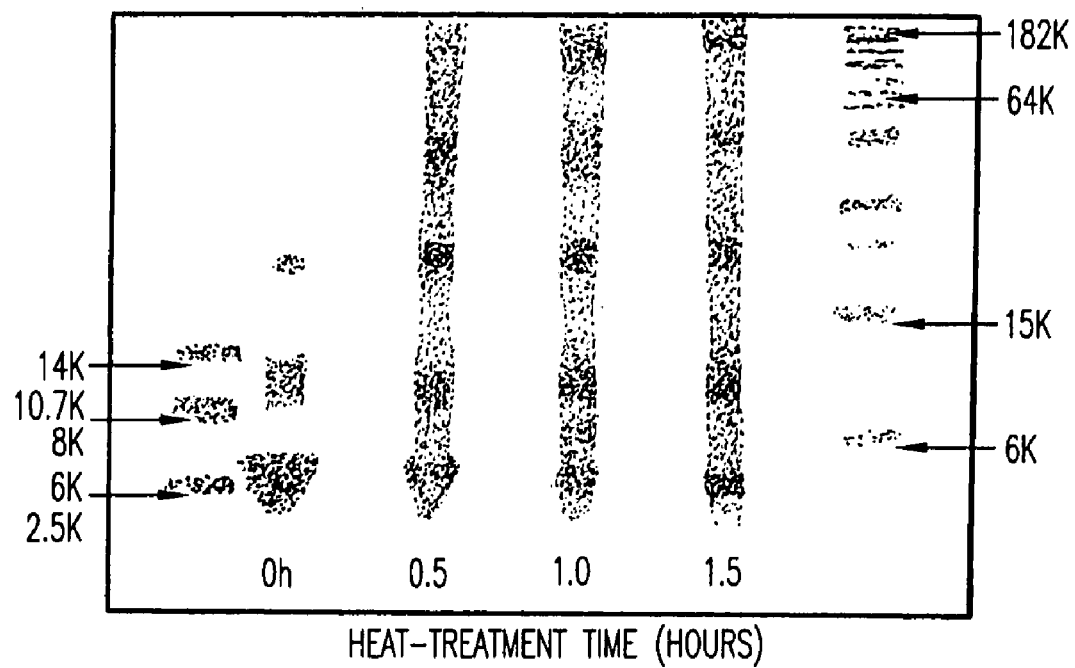
Figures 2, 6:
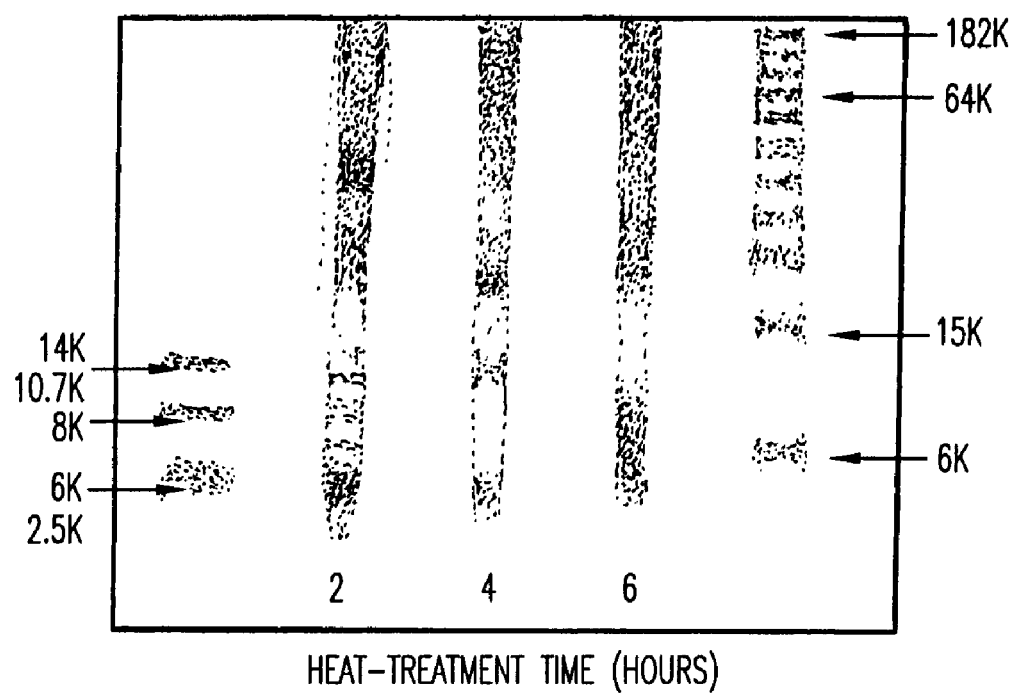

Powder of epsilon-poly-L-lysine having molecular weight of 4000 (Chisso Corporation, Lot No. 20211023F) was subjected to vacuum drying (heat treatment) at 180° C. Molecular weight of the heat-treated $\epsilon$-poly-L-lysine was evaluated by gel electrophoresis, in which adopted for the gel electrophoresis were 15% SDS polyacrylamide gel as electrophoresis gel as well as "Running buffer solution" (Nacalai Tesque, Inc.; 0.25 moL/L-Tris, 1.92 moL/L-glysine 10 g/L-SDS) as mobile phase. Gel electrophoresis apparatus of NIHON EIDO CO., LTD was used and gel electrophoresis is made under electric current of 50 mA. Adopted as markers were; "Peptide molecular weight marker" (Daiichi Pure chemicals Co., Ltd.; Mw=2,512 to 16,950; Lot No. 024RJZ) and "Protein Ladder" (Invitrogen Corporation; Mw=6,000 to 181,800; Lot No. 1283301A); and adopted as stain was "Coomassie brilliant blue" (Invitrogen Corporation; R-250). As a result, electrophoresis pattern as shown in FIG. 6 was obtained. For non-treated sample (time of the treatment is zero), main component appears between 2.5 k and 6K, as to accord with described value of the molecular weight, that is 4000, on a catalogue of Chisso Corporation. The other components were discontinuous, presumably due to association of the component having molecular weight of 4000. Heat treatment led to disappearance of spots and remarkable increase in molecular weight. Heat treatment exceeding 1.5 hours led to appearance of components exceeding the maximum molecular weight marker of 182K; and increase of heat treatment led to increase of high-molecular-weight components.

Heat-treated powders of the polylysine obtained in above were dissolved in distilled water as to prepare 10 wt % solutions while including 4 wt % of acetic acid, and thereby prepare the second liquids.

Figures 1, 7:
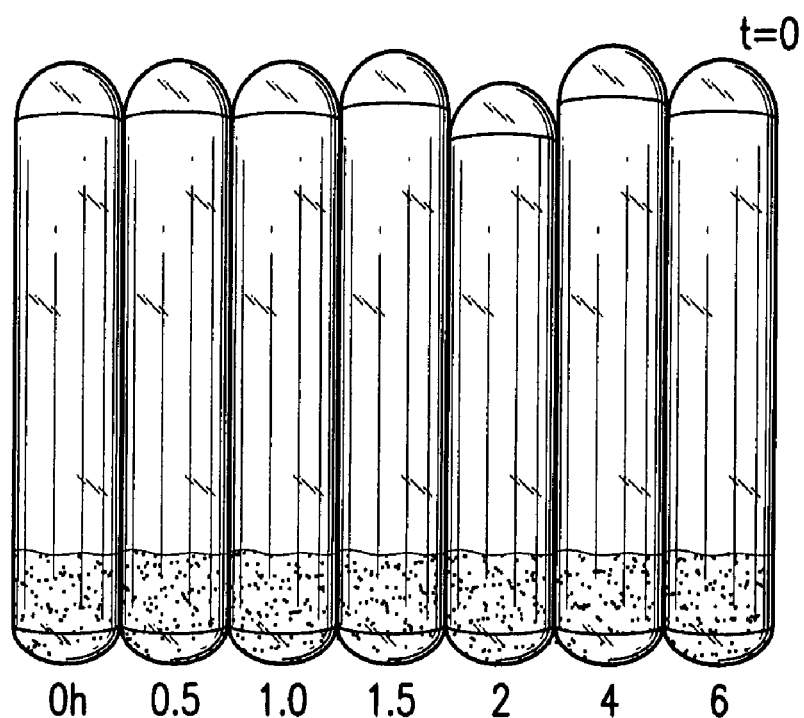
Figures 2, 7:
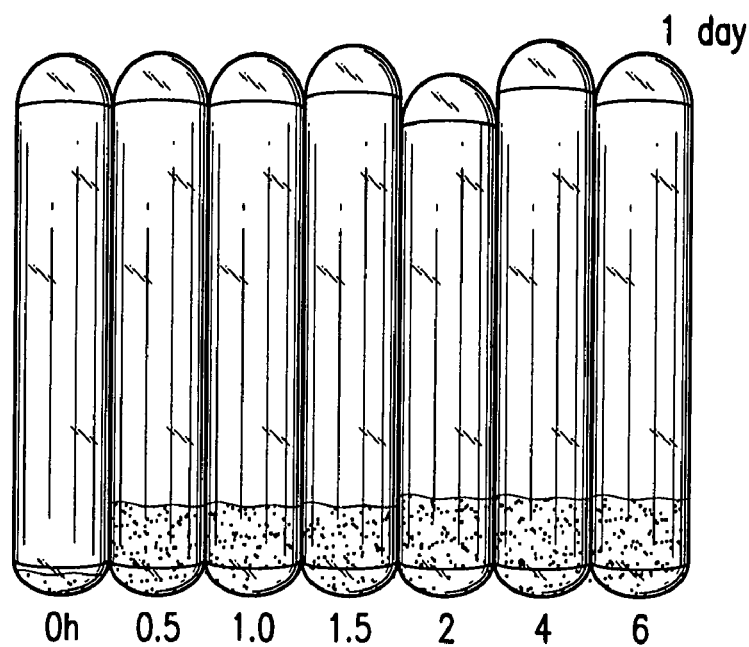
Figures 3, 7:
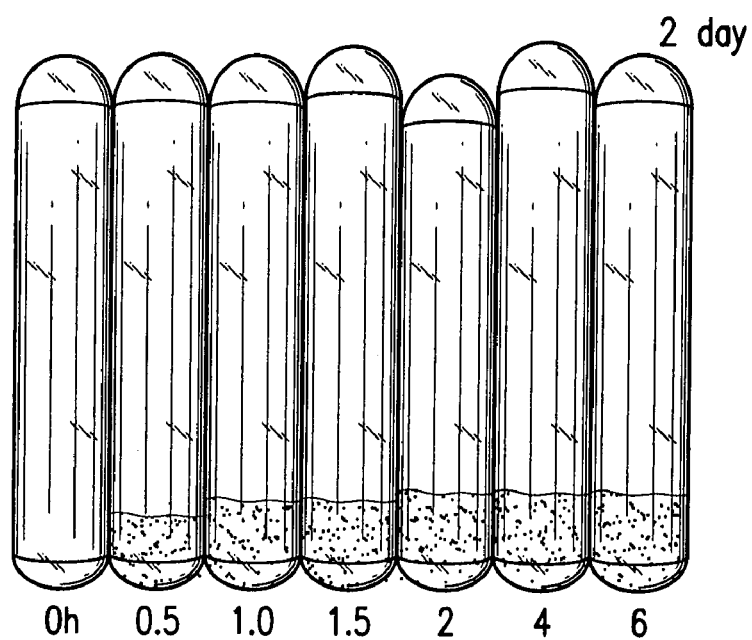
Figures 4, 7:
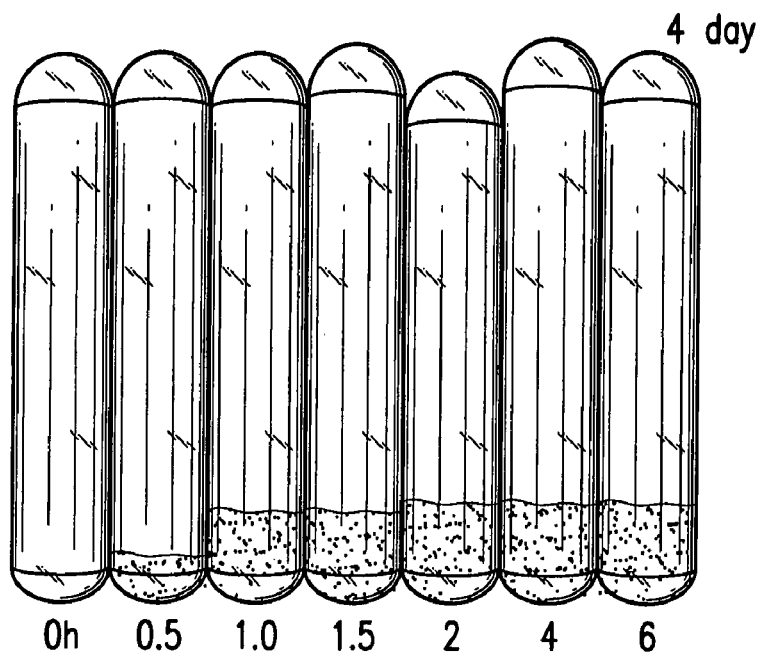
Figures 5, 7:
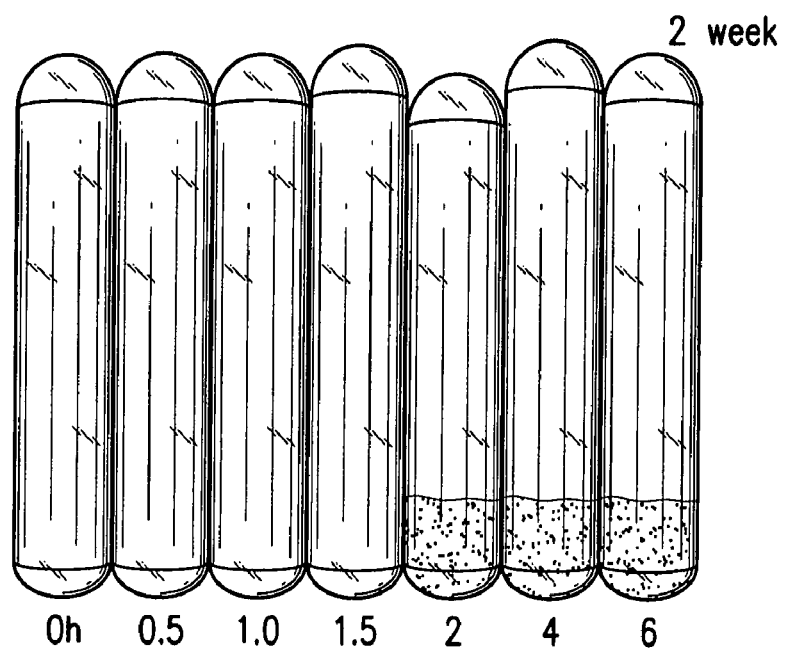
Figures 6, 7:
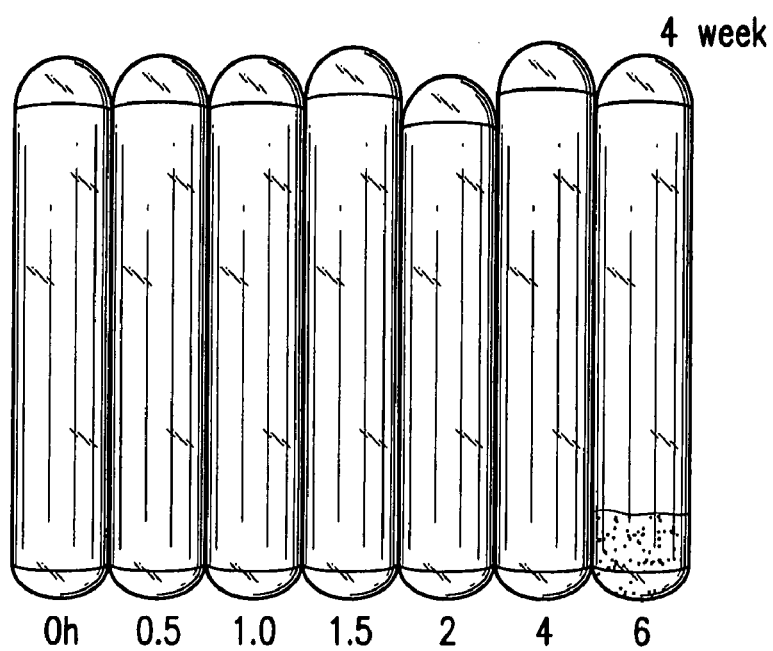

As the first liquid, the 20 wt % aqueous solution of dextran aldehyde having molecular weight of 75,000, which was used in Section 3, was adopted. After mixing the first and second liquids, disintegration rate of the cured adhesive was evaluated by the method described in Section 6. Results of the evaluation are shown in FIG. 7. Time period required for the disintegration increases with increase of the heat-treating time period and thereby with increase of molecular weight. When the heat-treating time period is zero, the cured adhesive was disintegrated by two days. When the heat-treating time period is 1.5 hours, two weeks was required for the disintegration; while 6 hours of the heat treating made require no less than one month for the disintegration.

As mentioned in Section 8, disintegration time period of the cured resin may be easily delayed by selection of pH adjuster (among acetic acid, citric acid and so on). Hence, it is considered that adopting of ϵ-poly-L-lysine without heat treating enables controlling of the disintegration time period freely in a range from short time up to a long time. On contrary, when adopting of ϵ-poly-L-lysine having been subjected to long heat treatment, it is considered that such controlling becomes difficult. However, heat treatment of around 0.5 hour or less, at 180° C., for example would be adoptable as a way for controlling the disintegration time period.

Taking account of results in Section 6, in which the chitosan having molecular weight of 100,000, would lead following; molecular weight of the amino-group-containing polymer have to be no more than dozen thousands in order to achieve sufficient self-disintegration of the invention.

10. Applying of Electron Radiation Sterilization

As the first liquid, the 20 wt % aqueous solution of dextran aldehyde having molecular weight of 75,000 used in Section 3 was adopted. The 10 wt % neutral polylysine aqueous solution same as in Section 3 was prepared and used as the second liquid. The first and second liquids are filtered through a syringe filter (Dismic 25AS020AS; ADVANTEC MFS, INC or Toyo Roshi Kaisha, Ltd.) having apertures of 0.2 μm diameter then be respectively charged into 5 mL glass ampoules, which are then sealed. For each pair of the first and second liquids, sterilization was made at 25° C. under condition shown in left-hand end of Table 5. After sterilization, curing time was measured by the method shown in Section 2 as to reveal effect of the sterilization. These results are shown in Table 5.

TABLE 5

Varying of curing time due to radiation irradiation

| Sterilization | Curing time/second* | Difference/second |
|---|---|---|
| No sterilization | 13.04 ± 0.20 | 0 |
| Gamma radiation (25 KGy) | 13.65 ± 0.06 | 0.62 |
| Electron radiation (20 KGy) | 10.66 ± 0.26 | −2.38 |
| Electron radiation (40 KGy) | 8.25 ± 0.07 | −4.79 |

*data = average ± S.D. (n = 3)

As shown in the table, the gamma radiation induced a slight delay of the curing while, on contrary, the electron radiation induced shortening of the curing time. Thus, it is presumed that the electron radiation induces neither decrease of molecular weight nor alteration in respect of each component of the adhesive and has wide variety of applicability as a way for sterilization of the adhesives of the invention.

11. Softness Evaluation of the Cured Adhesive by Compression Test

Figure 8:
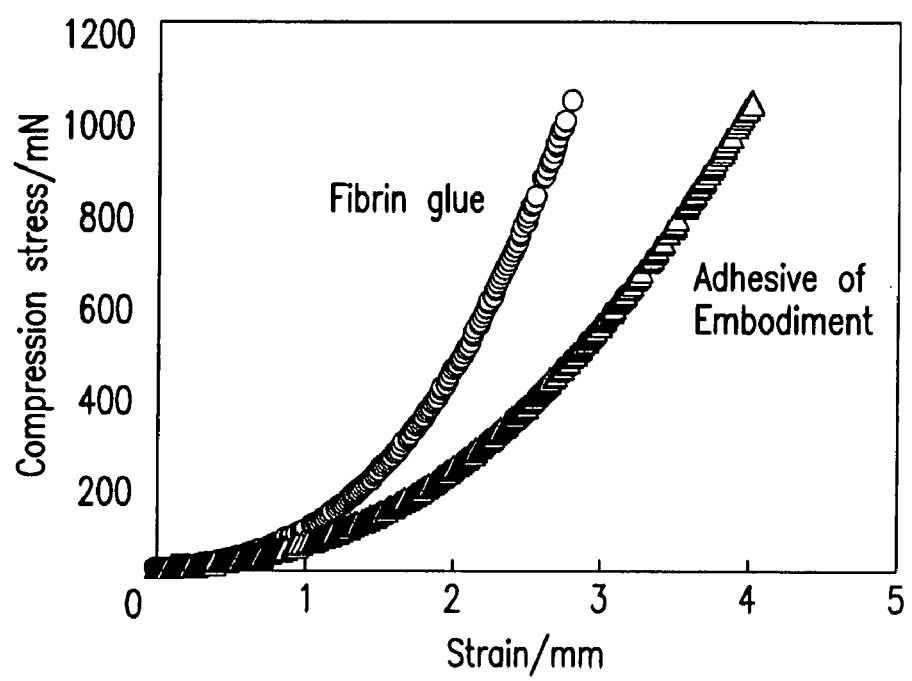
FIG. 8 shows stress-strain curves for the cured resins of the adhesives (Section 11)

As the first liquid, the 20 wt % aqueous solution of dextran aldehyde having molecular weight of 75,000 used in Section 3 was adopted. The 10 wt % neutral polylysine aqueous solution same as in Section 3 was prepared and used as the second liquid. The first and second liquids were mixed with each other by the mixing apparatus dedicated to such mixing; and 2 mL of thus obtained mixture was poured into each well having 2 cm$^2$ of bottom area, on a 24-well plate for cell culture. After leaving at 25° C. for 2 minutes, a hemisphere having diameter of 6.6 mm was pressed onto the cured adhesive at a rate of 10 mm/min by use of a tensile test machine (ADS-5D of SHIMADZU CORPORATION), as to measure compression stress and thereby to evaluate pliability of the cured resin. As a comparative adhesive, the fibrin glue ("Bolheal", KAKETSUKEN in Japan) was subjected to an evaluation procedure same as above. FIG. 8 shows stress-strain curve of the results.

In the figure, each plot represents a penetration distance (mm), by which the hemisphere was penetrated into the cured resin, and a corresponding stress value (mN). Inclination of a plotted curve for the adhesive of the embodiment is as much as about half of that for the fibrin glue, in a region at afterward of about 1 mm of the penetration distance, while initial inclinations of the two curves make only a small difference. This result indicates that the cured adhesive of the invention is softer than cured fibrin glue.

Though data is omitted here, the strain-stress curve of the adhesive of the invention at the compression test was varied by modifying the addition amounts of sodium periodate into 3 g or 10 g, with respect to 20 g of dextran. Hence, by modifying of extent of the aldehyde groups introduction, cross-linkage density at a time of the curing is freely changed as to freely control softness of the cured gel resin layer.

12. Evaluation of Adhesion Strength by Use of Cattle Leather

As the first liquid, the 20 wt % aqueous solution of dextran aldehyde having molecular weight of 75,000 used in Section 3 was adopted. The 10 wt % neutral polylysine aqueous solution same as in Section 3 was prepared and used as the second liquid. In other words, the adhesive of Reference Example 3 was adopted. Adhesion test was made by using cattle leather as adherents for evaluating adhesion strength of the adhesive. Cattle leather (TRUSCO Corporation; JT-5L, long-sleeve leather glove for worker) is sliced to strips of 1 cm×5 cm; and a pair of leather strips was bonded by an adhesion area of 1 cm×1 cm and was then left to stand still under 100 g of load as to achieve the curing. Thus obtained bonded pair of strips was subjected to shear adhesion strength test by use of the tensile test machine used in Section 11 and by causing shear motion at a rate of 10 mm/min; and adhesion strength at a time of peeling apart was obtained (n=5). As a comparative adhesive, the fibrin glue ("Bolheal", KAKETSUKEN or The Chemo-sero-therapeutic Research Institute, in Japan) was subjected to an evaluation procedure same as above.

Resultantly, adhesion strength was 2024±563 g/cm$^2$ for the adhesive of the embodiment (Reference Example 3) and was 519±136 g/cm$^2$ for the fibrin glue. As for the adhesive of the embodiment, its average adhesion strength was about 4 times of that of the fibrin glue and most of samples exhibited adhesion strength no less than 1 kg/cm$^2$. On contrary, adhesion strength of the fibrin glue was generally low and varied widely, due to too short curing time and thereby to difficulty in preparing the bonded samples. Curing time measured by a method of Section 2 was about 10 seconds for the adhesive of the embodiment and was no more than a second for the fibrin glue.

13. An Example of Use on Digestive Surgery—Haemostasis on Liver

As the first liquid, the 20 wt % aqueous solution of dextran aldehyde used in Section 4 was adopted. Adopted respectively as the second liquids were; the 20 wt % neutral polylysine aqueous solution and the 50 wt % two-functional PEG-$NH_2$ (free amine) aqueous solution, both of which had been obtained at Section 2. The adhesive adopting the neutral polylysine aqueous solution as the second liquid is equivalent to the adhesive of the Example 1 in Section 2.

Abdominal cavity of a domestic rabbit that had been sacrificed was opened along a median line as to expose a liver. By use of a surgical scalpel, a wound (incision) of about 2 cm length and about 5 mm depth was made as to cause continuous bleeding from the incision. Subsequently, the first and second liquids were mixed by equal volumes, by use of a mixing device dedicated to such mixing; and the mixture was applied on the incision.

Figures 1, 9:
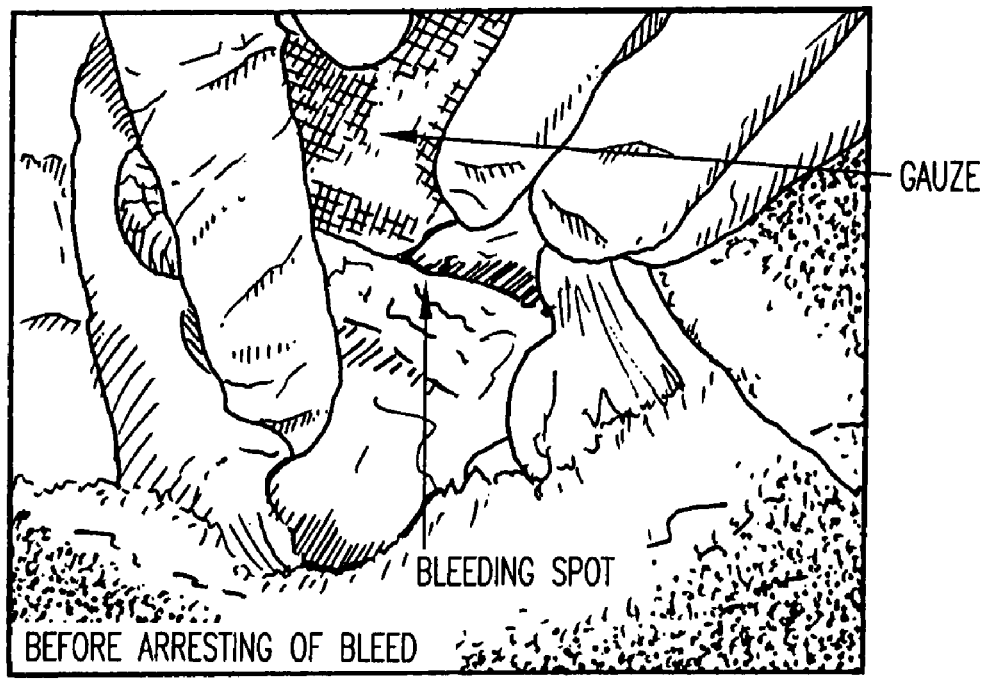
Figures 2, 9:
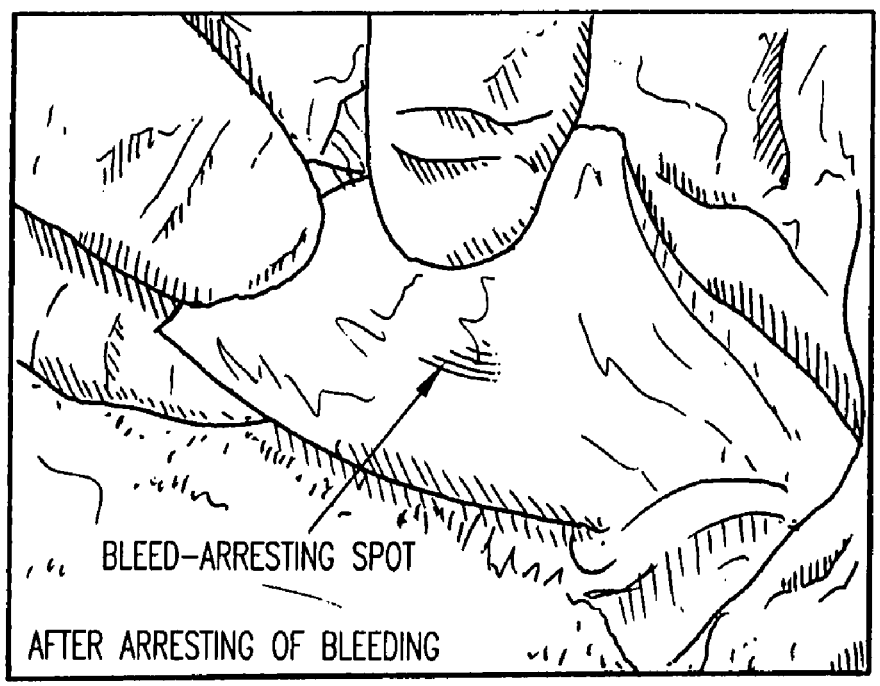

Resultantly, a reliable arrest of bleeding was observed; within 10 seconds by the adhesive (Example 1) adopting the neutral polylysine aqueous solution as the second liquid; and within 30 seconds by the adhesive adopting the two-functional PEG-$NH_2$ aqueous solution as the second liquid. FIG. 9 shows the liver before and after the haemostasis by use of the adhesive adopting the polylysine solution as to indicate achieving of effective haemostasis. Moreover, a film of the adhesive was firmly fixed on the liver. Hence, it was revealed that the adhesive of this example exhibits excellent effect as haemostasis agent in digestive surgery.

14. An Example of Use on Cardiovascular Surgery—Prevention of Tissue Adhesion

As the first liquid, the 20 wt % aqueous solution of dextran aldehyde having molecular weight of 75,000 used in Section 3 was adopted. The 10 wt % neutral polylysine aqueous solution same as in Section 3 was prepared and used as the second liquid. In other words, the adhesive of Reference Example 3 was prepared.

Meanwhile, 20 g of dextrin having molecular weight of 7000 (Wako Pure Chemical Industries, Ltd; Lot No. EWQ7180) was reacted with 5 g of sodium periodate; and dextrin aldehyde (aldehyde-groups-containing dextrin) was obtained by the method of Section 2. Subsequently, 20 wt % aqueous solution of the dextrin aldehyde was prepared and used as the first liquid of the adhesive. And, 10 mL of 25 wt % polylysine aqueous solution that was used in Section 2 was added with 0.5 mL of succinic anhydride and 14.5 mL of distilled water as to prepare 10 wt % neutral polylysine aqueous solution, which was used as the second liquid. Thus, a dextrin-based example of the two-part adhesive was obtained.

In order to confirm adhesion-prevention effect in cardiovascular surgery, pericardium of a rat was cut as opened. Then, surface of left ventricle was rubbed 100 times with a gauze pad as to make a condition for inducing the tissue adhesion. The rubbed surface was coated with each of the adhesives of various compositions; and then thorax was closed up. Four weeks later, the thorax was opened up and extent of tissue adhesion was evaluated (n=5) by 5 scales as to be ranked at either of 0, 1, 2, 3 and 4, in which larger number indicates higher extent of tissue adhesion. As an adhesive of a comparative example, fibrin glue ("Bolheal", KAKET-SUKEN in Japan) that has been in clinical use as tissue-adhesion inhibitor was adopted. Obtained scales are as follows: 2.4±0.5 for non-treatment; 1.2±0.4 for fibrin glue; 3.2±0.4 for the adhesive of the Reference Example 3 (Section 3); and 1.2±0.4 for the dextrin-based adhesive of the embodiment.

Disintegration rate evaluation according to the method of Section 6 revealed the disintegration period of; one month for the adhesive of the Reference Example 3 (Section 3); and 2 to 3 days for the dextrin-based example of the adhesive. These results revealed that disintegration of the dextrin-based example of the adhesive is extremely rapid. In view of these and foregoing results, tissue adhesion would be severer when the adhesive having a long disintegration period was used than when no adhesive is applied; and extent of the tissue adhesion at an occasion the gel of the adhesive (Reference Example 3) having a short disintegration period was used was almost same with that at an occasion fibrin glue was used. Thus, it was revealed that the adhesive having a short disintegration period is highly effective for curbing tissue adhesion on the heart.

Figures 1, 10:
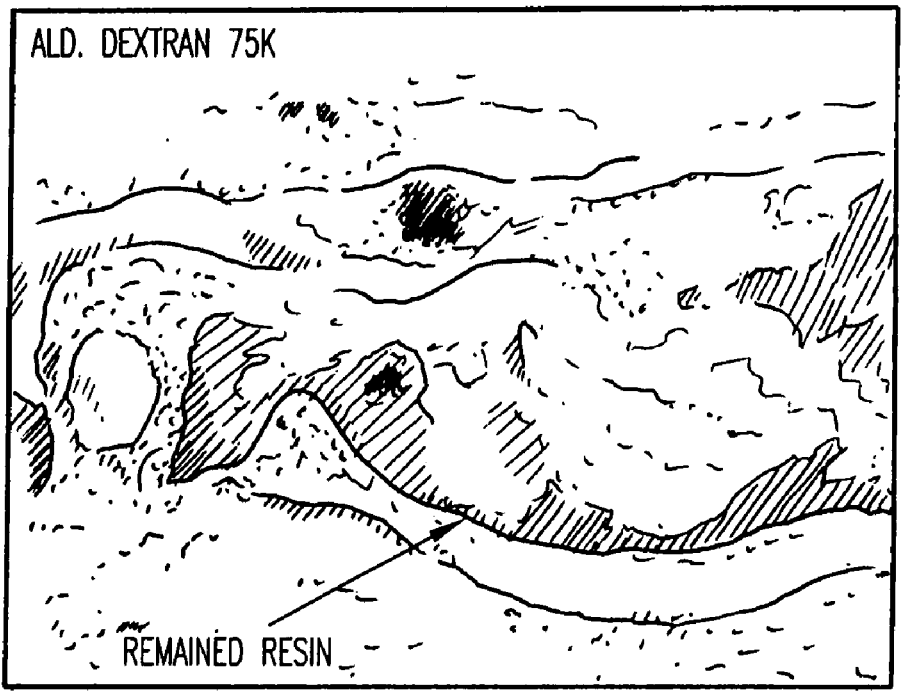
Figures 2, 10:
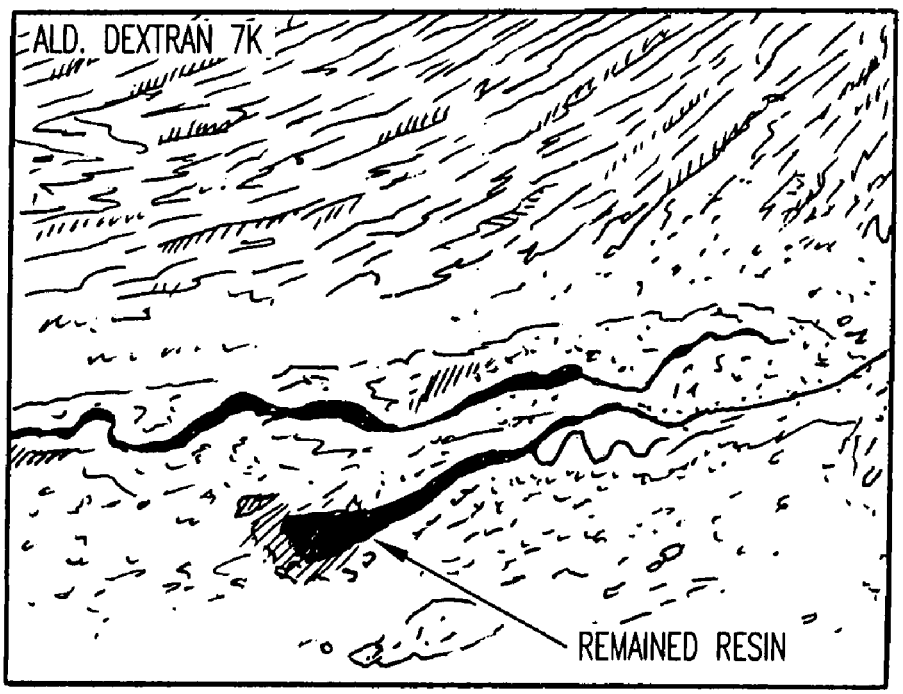

Each of FIGS. 10-1 and 10-2 shows an image of a tissue section that has been stained with Masson-Trichrome and taken from an affected part 4 weeks after surgery. As indicated by an arrow in the figure, remaining of the cured resin is seen on the image. At a time of surgery, epicardium on surface of the heart was rubbed by a gauze pad as to make a wound and thereby a tissue-adhesion-induced area. By such rubbing, the epicardium there was presumably ripped out near completely, as to expose cardiac muscles; and coating by the adhesive was made on such exposed part. A tissue enclosing the adhesive was formed after the coating. While amount of the coating was same between the adhesives, remaining amount of cured resin was very small for the dextrin-based adhesive of the embodiment due to high disintegration rate, compared to an occasion the adhesive of the Reference Example 3 was used. Presumably due to this, tissue adhesion was slight when the dextrin-based one was used. Hence, it is revealed that the adhesives of the invention are effective as the tissue-adhesion inhibitor for cardiovascular surgery because disintegration rate is easily controlled.

15. Other Example of Use on Cardiovascular Surgery—Haemostasis

The 20 wt % dextran aldehyde aqueous solution that had been used in Section 8 was prepared by use of dextran having molecular weight of 40,000, and was used as the first liquid. The 20 wt % neutral polylysine aqueous solution used in section 8 was prepared and used as the second liquid (4% citric acid content). In other words, a two-part adhesive equivalent to the Reference Example 3 was prepared. The adhesive of Reference Example 3 has almost same property and performance with the adhesive of the Examples except that; disintegration is somewhat slower in the Reference Example 3 than in the Examples.

Following experiment was made for confirming haemostasis effect in cardiovascular surgery.

Anesthesia is made by follows; a rat is left in an ether atmosphere for 30 seconds, then a tube is inserted into a bronchus and making the rat inhaling isoflurane. Free wall of left ventricle of the rat was sutured up as to halt blood flow, and a pinhole was opened by picking with a 19-gage needle. Suture was temporarily loosen as to confirm occurrence of pulsative bleeding and then stitching up was made again to completely interrupt blood flow. Blood around the pinhole was removed, and a paper having a hole slightly larger than the 19 gage was put on the heart as to prevent flowing out of blood and the adhesive to surrounding.

Onto the pinhole, 0.4 mL of the adhesive was applied by use of a syringe that is for injecting insulin. Three minutes later, a gauze pad was put on as to absorb oozed-out blood. Then, the suture was loosen and kept loosen for three minutes. Here, weight of the gauze pad had been measured on before hand, and weight increase after absorption of blood was taken as amount of bleeding. For comparison, fibrin glue ("Beriplast", KAKETSUKEN in Japan) was tested in same manner with above. Numbers of rats used for this experiment were 6 for non-treatment, 5 for the adhesive of the embodiment and 5 for the fibrin glue.

Amounts of bleeding were 1.1±0.5 g for non-treatment, 0.4±0.1 g for the adhesive of the embodiment and 0.9±0.5 g for the fibrin glue. The amount of bleeding for the adhesive of the embodiment was significantly smaller (p=0.02) than that for the fibrin glue. When the fibrin glue was used, two ways of bleeding were observed; by breaking out through the cured resin and by oozing through a fissure between periphery of the cured resin and a tissue. When the adhesive of the embodiment was used, bleeding only by oozing through the fissure was observed and amount of the oozing was small. Such difference of manner of bleeding is presumed to cause difference in amount of bleeding. Thus, the adhesive of the embodiment was revealed to be effective as haemostasis agent for cardiovascular surgery.

16. An Example of Use in Respiratory Surgery—Obturation of Air Leakage from Lung As the first liquid, the 20 wt % aqueous solution of dextran aldehyde having molecular weight of 75,000 used in Section 3 was adopted. The 10 wt % neutral polylysine aqueous solution same as in Section 3 was prepared and used as the second liquid. In other words, the adhesive of Reference Example 3 was prepared.

To confirm obturation of the air leakage from lung, following experiment was made by use of a beagle dog. In accordance with common procedures, conducted were anesthesia, endotracheal intubation, and then opening of thorax; and a pleural deficient area of 3 cm×3 cm was cut out on right lung by use of an electrical scalpel. Physiological saline was sprayed on the deficient area, and pressure of respirator was increased, as to confirm occurrence of air leakage. Subsequently, by use of a mixing device dedicated to mixing of two-part liquids, about 2 mL of the adhesive was dropped on the deficient area and rubbed to be spreaded thereon with fingers for 10 seconds. Two minutes later, thorax was filled with physiological saline and a leakage test was made. As a comparative adhesive, the fibrin glue ("Bolheal", KAKETSUKEN in Japan) was used and fibrinogen solution was rubbed to be spreaded on the deficient area by fingers and then further applied thereon by use of a sprayer kit (rub & spray method). In regard of using of fibrin glue, leakage test was made 5 minutes after the application, in accordance with science literature(s).

Figures 1, 11:
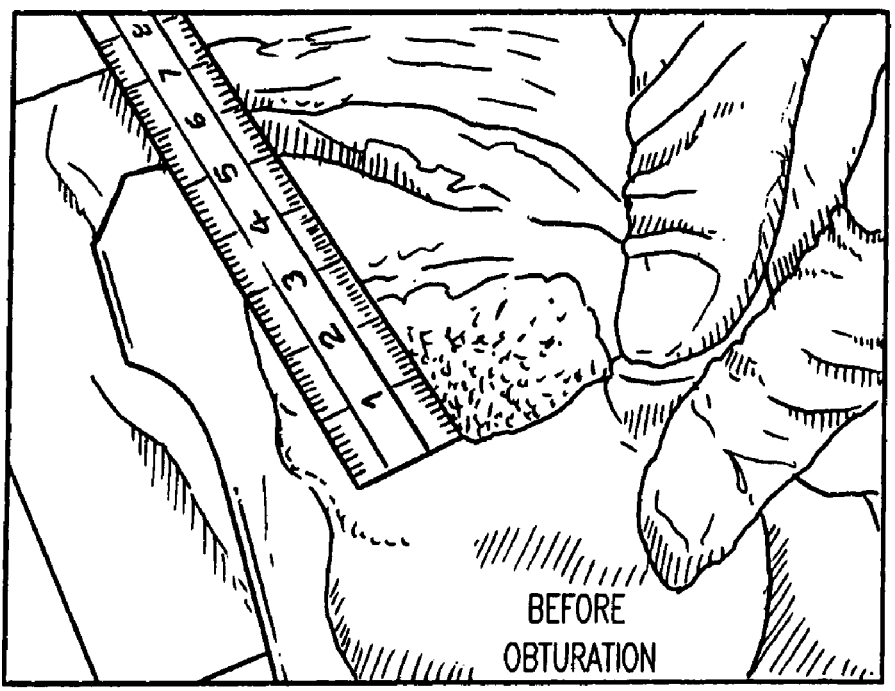
Figures 2, 11:
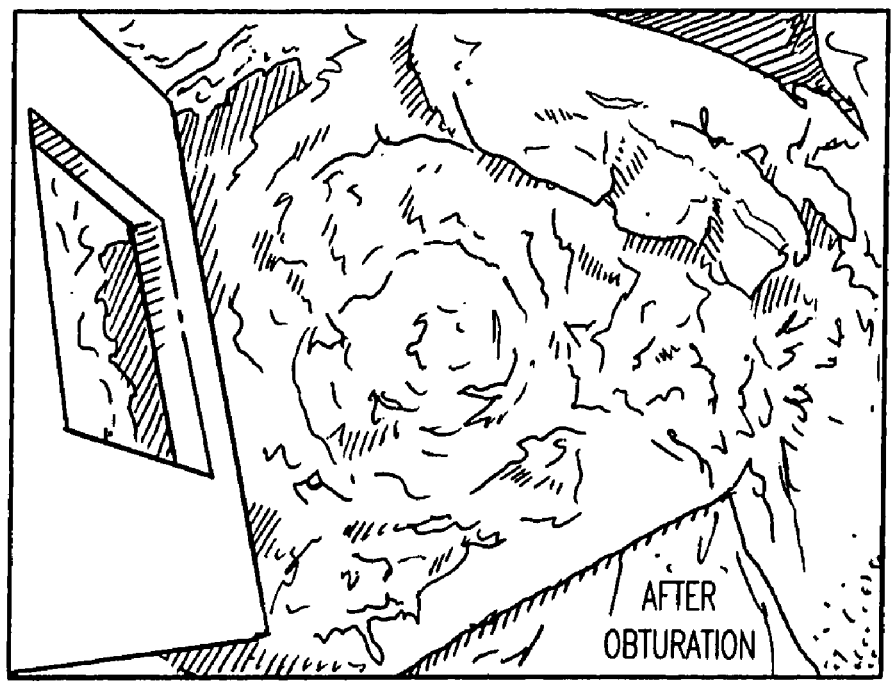

Pressure at which air leakage was observed was 35.4±6.8 cmH$_2$O for the adhesive of the embodiment and was 33.3±4.8 cmH$_2$O for the fibrin glue ("Bolheal"), and thus no big difference was recognized between them. Nevertheless, manners of air leakage greatly differed. As for fibrin glue, fibrin mass as a whole was peeled off from the lung as to expose the deficient area and thereby cause the air leakage (with large bubble). By the adhesive of the embodiment, the deficient area was surely kept. Pinholes are formed around the cured adhesive, and only very small bubbles were observed. FIGS. 11-1 and 11-2 show surface of the lung respectively before and after coating of the adhesive of the embodiment and indicates that the deficient area is covered by the cured adhesive as a result of the coating of the adhesive. Progresses after the surgery were observed to be favorable both by the adhesive of the embodiment and by the fibrin glue. Theses results indicated that the adhesive of the embodiment is highly effective in respiratory surgery on purpose of air leakage obturation.

17. Reference Example 1—Polyethylene Glycol Having End Amino Groups

The 20 wt % dextran aldehyde aqueous solution obtained at Section 4 (molecular weight of dextran is 40,000) was used as the first liquid. As the second liquid, adopted was the 50 wt % aqueous solution of polyethylene glycol amine having an amino group on each of two ends (two-functional PEG-NH$_2$, free amine) and having molecular weight of 3000, which was obtained by dissolving in distilled water as Section 2.

Subsequently, time course of disintegration of the cured adhesive was observed by a method described in Section 6. Resultantly, the cured adhesive was completely fluidized three hours after the curing. The two-functional PEG-NH$_2$ has amino groups only on two ends even though having molecular weight of 3000, and hence, reaction takes place on the two ends. Thus, density of cross linkage would become very small; and this is presumed to be cause of rapid disintegration.

By results of this section and results of Section 2 on polyethylene glycol amine, it is supported that the amino-group-containing polymer has to be a polymer chain of amino-group-containing units.

18. Reference Example 2—Chitosan Oligosaccharide

The 20 wt % dextran aldehyde (MW 40,000) aqueous solution obtained at Section 4 was used as the first liquid. Meanwhile, powder of low-molecular-weight chitosan ("Y.H. Chitosan Oligosaccharide", YAEGAKI Bio-industry, Inc.; Lot. 000522; lactate, mixture of di- to hexa-saccharides, MW 700) was dissolved in distilled water as to prepare 50 wt % aqueous solution, which was used as the second liquid.

Subsequently, the first and second liquids were mixed in a test tube for the reaction as in same manner with the Reference Example 1; and no curing was made even 7 hours later. Because of this, the test tube was further charged with 1 mL of the first liquid and with 100 mg of the powder of "Y.H. Chitosan Oligosaccharide" instead of the second liquid. Curing was observed 30 minutes later. Then, 3 mL of phosphate buffer solution was added into the test tube, which was then sealed. And, time course of disintegration of the cured resin was observed. Resultantly, the cured resin was completely fluidized by 6 hours. Such rapid disintegration and fluidization are presumably due to follows. The "Y.H. Chitosan Oligosaccharide" has too low molecular weight, although having one amino group at each unit of sugar residue. Hence, gel would not be formed by use of 50 wt % solution. Even by using of powder of the "Y.H. Chitosan Oligosaccharide", effective gel network structure would not be formed.

Results of using the chitosan oligosaccharide reveal that; molecular weight of a chain polymer of amino-group-containing units has to be at least 1000 when for achieving proper disintegration time period of one day or more. Results of using the chitosan oligosaccharide induce the assumption that; low-molecular-weight chitosan would make a behavior similar with that of the low-molecular-weight polylysine or the like. Hence, when taking account of results of Section 6 for chitosan addition, it is conceived that; the advantageous effect peculiar to the invention would be obtained only when molecular weight of chain polymer of the amino-group-containing units is in a range 1000 to 20,000.

EMBODIMENTS OF THE SECOND ASPECT

Powder-Liquid Medical Adhesive

A1. Preparation of Powder Dextran Aldehyde (the First Part)

Twenty grams of dextran (Wako Pure Chemical Industries, Ltd; Lot No. EWK3037) having weight-average molecular weight of 75,000 was dissolved in 100 ml of distilled water. Then, obtained solution was added with 3 g of sodium periodate (MW 213.89) and stirred at 40° C. for 5 hours as to proceed reaction. After the reaction, product solution was subjected to dialysis for 24 hours by use of distilled water and dialysis membrane of fractioning molecular weight of 14,000, and thereafter being freeze dried. Subsequently, dried product was subjected to pulverization for 1 minute by use of a portable crusher ("Wonder Blender WB-1" of OSAKA CHEMICAL Co., Ltd.), as to obtain the dextran aldehyde in a form of powder.

The amount of the introduced aldehyde groups per anhydroglucose unit (mole) was 0.28. This measurement was made by the redox titration method, detail of which is same as described in Section 1 of the Embodiments of the First Aspect.

Figure 12:
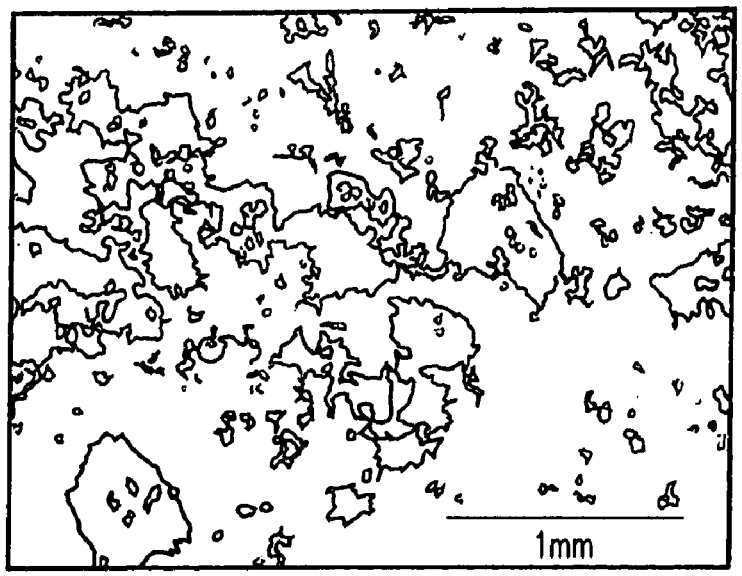
FIG. 12 is a photomicrograph showing powder-form first part of the adhesive.

Particle sizes of the powder were evaluated by stereomicroscope as to reveal that; the powder has an average particle diameter of about 90 micrometer as shown in a photograph of FIG. 12. Moreover, electron microscope observation on surface of the powder revealed porous nature of the powder.

A2. Preparation of Epsilon-Polylysine Aqueous Solution (the Second Part)

The 25 wt % polylysine aqueous solution (molecular weight of 4000; Chisso Corporation, Lot No. 2050506, free amine) used in Section 2 was added by acetic anhydride and distilled water, in a manner that concentration of the acetic anhydride becomes 2 wt %, as to prepare 10 wt % polylysine neutral aqueous solution.

A3. Preservation Stability of the Dextran Aldehyde

The powder dextran aldehyde obtained in Section A2 was put in polyethylene bottles and kept respectively at −20° C. and at +50° C. At an elapse of 40 days, the two samples of the powder were subjected to molecular weight analysis by use of GPC device; and peaktops of obtained curves indicated a molecular weight of 19,223 for a sample having been kept at −20° C. and a molecular weight of 18,659 for a sample having been kept at +50° C. In other word, no deterioration due to high temperature storage was observed. Meanwhile, the dextran aldehyde same as above was dissolved to prepare 20 wt % aqueous solution, which was then kept at +50° C.; and molecular weight analysis as in the above reveals that 14 days and 28 days storage caused drops of molecular weight respectively to become 80% and 70% of the original one. On the other hand, each of the aqueous solutions of the dextran aldehyde was mixed with the 10 wt % polylysine neutral aqueous solution obtained at Section A2; and curing (gelling) time of the mixture was measured as to evaluate extent of deterioration of the dextran aldehyde. Result of such evaluation shows that elapse of 14 days and 28 days at +50° C. respectively correspond roughly to 1 year and 3 years at 25° C.

A4. Sealing Performance

The powder dextran aldehyde obtained at Section A1 and the neutral polylysine aqueous solution obtained at Section A2 were used to form a hydrogel and to evaluate sealing performance of the hydrogel. Details of procedures were as follows.

Figure 13:
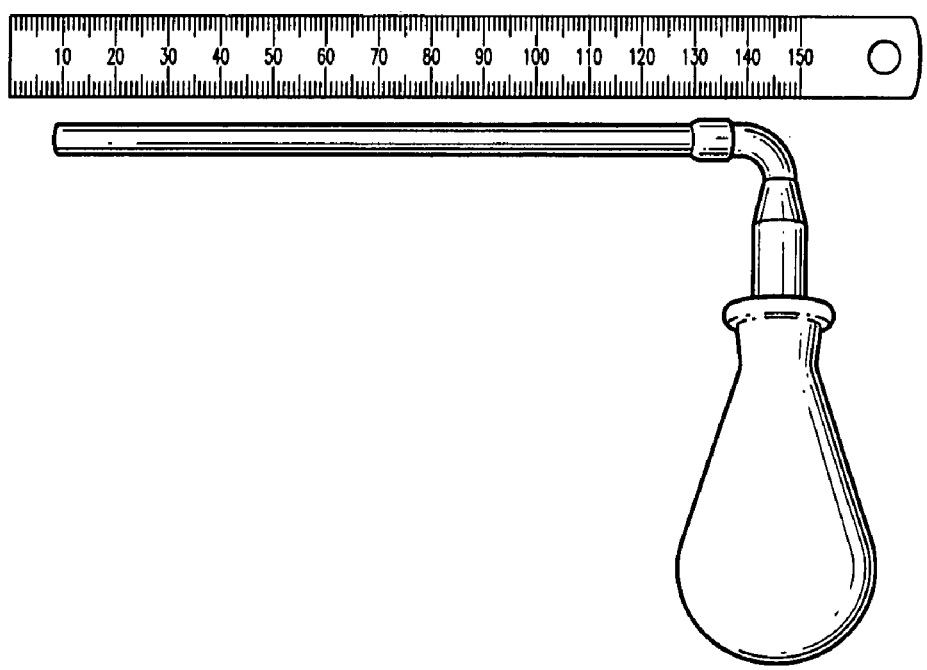
FIG. 13 is a photograph showing a hand-made powder-spraying device prepared by use of a dropper cap.
Figure 14:
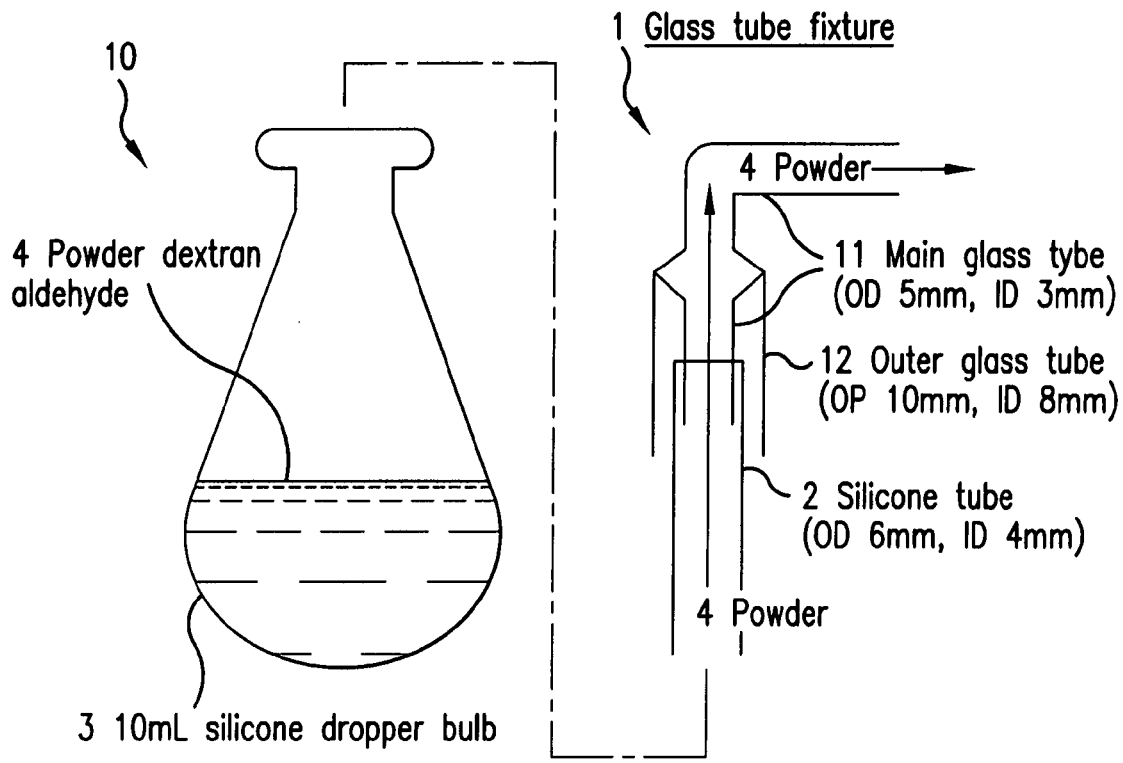
FIG. 14 is a schematic illustration of the device shown in FIG. 13.

Firstly, a hand-made powder-spraying device 10 was prepared by use of a dropper cap, as shown in a photograph of FIG. 13 and a schematic illustration of the device, of FIG. 14. In detail, a main Pyrex glass tube 11 having outer diameter of 5 mm and inner diameter of 3 mm was bent by heating almost perpendicularly; a silicone tube 2 having outer diameter of 6 mm and inner diameter of 4 mm was attached on an end of the main Pyrex glass tube 11; and an outer Pyrex glass tube 12 having outer diameter of 10 mm and inner diameter of 8 mm was fusion bonded on a portion of the main Pyrex glass tube 11, as to form a glass tube fixture 1. A silicone-rubber dropper bulb 3 having a 10 ml volume was charged with about 3 g of the dextran aldehyde powder 4 and then securely attached on the outer Pyrex glass tube 12 of the glass tube fixture 1.

A cap formed of polyethylene and having diameter of 37 mm and height of 20 mm, of a bottle for chemicals, was perforated at its center to form a hole in a diameter of 10 mm, and then placed on a laboratory bench in a manner that inner face of the cap was exposed upward. Then, 0.5 g of the powder-form first part of the adhesive was thinly and almost evenly sprayed on the inner face of the cap, by use of the powder-spray device 10. Subsequently, 0.1 g of the liquid-form second part of the adhesive was sprayed thereon; and the 0.5 g of the powder-form first part of the adhesive was thereon applied by use of the powder-spray device. Obtained gel was gelatinous and fully flexible. Two minutes later, the cap was screwed to be fixed on main part of the bottle for chemicals, which is formed of polyethylene and has a volume of 500 mL and a height of 175 mm. On beforehand of the screwing, bottom part of the bottle had been cut out. The bottle having been screwed with the cap was overturned and water was slowly poured into a barrel part of the bottle. Resultantly, pouring of 500 g water did not cause rupture of the gel and leakage of water. Thus, high level of sealing or water-tight performance was confirmed.

A5. Adhesiveness and Flexibility

Adhesiveness on a tissue and flexibility was evaluated for the adhesive resin using the powder dextran aldehyde obtained in Section A1 and the neutral polylysine solution obtained in Section A2. In detail, a beagle dog under anesthesia was intubated and its lung was exposed while motion of the lung was maintained with artificial respirator. On surface of the lung, 1 g of the powder-form first part of the adhesive was thinly and almost evenly sprayed by use of the powder spray device used in Section A4. Then, 0.5 g of the liquid-form second part of the adhesive was almost evenly dropped thereon. Further thereon, 1 g of the powder-form first part was sprayed in same manner as above. Two minutes later, a pressure was applied to the lung by supplying oxygen through the airway (respiratory tract). And, it was examined whether the gel was peeled off from the lung surface. Resultantly, no peeling off from the lung surface was observed even under pressure of 40 cmH$_2$O or more. Moreover, repeating of inflation and deflation of the lung did not cause rupture of the gel, as to confirm a high level of flexibility of the gel.

A6. Haemostasis on Liver

Oozing of blood from a partially cut out portion of the liver was arrested by use of the adhesive formed of the powder dextran aldehyde of Section A1 and the neutral polylysine solution of Section A2, as follows in detail. After an artery in the liver was ligated, the liver was partially cut out by use of a forceps, as to expose a cut-out surface. On course of such cutting, blood vessels were cut off by use of an electric scalpel; and cutting off of each blood vessel having diameter more than 1 mm was made only after its litigation. The cut-out surface 5 arranged substantially vertical, which is an increscent half-moon or first-quarter-moon area on center of photograph of FIG. 15, was thinly and almost evenly sprayed with 2 g of the powder-form first part of the adhesive by use of the powder spray device in Section A4. Subsequently, 1 g of the liquid-form second part of the adhesive was almost evenly sprayed thereon, by use of a fibrin glue spray device ("Bolheal spray set" of TEIJIN PHARMA LIMITED), which is a double-syringe and air-driven spray device. Further, 2 g of the powder-form first part of the adhesive was sprayed on the cut-out surface.

Figure 15:
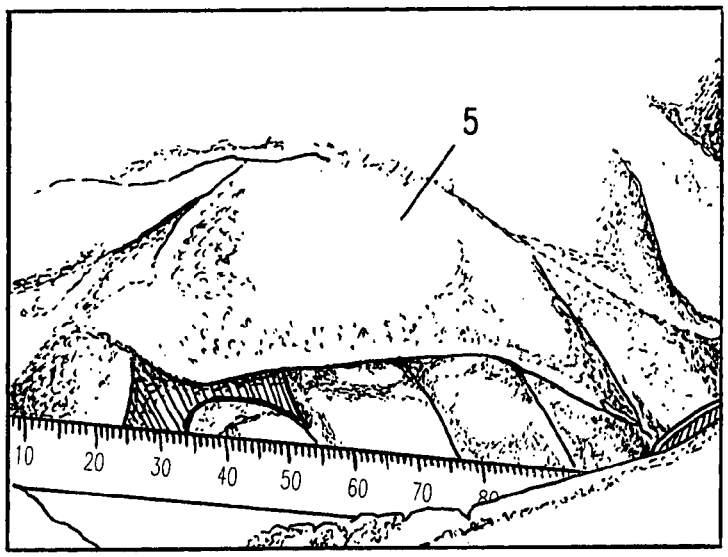
FIG. 15 is a photograph showing that bleeding on liver has been arrested.

Two minutes later, the cut-out surface 5 having been arrested of bleeding was applied with a gauze pad, weight of which had been measured on beforehand, and then, litigation of the artery was undone so that bleeding amount was obtained by measuring of the gauze pad soaked with blood. Resultantly, only 1 g of bleeding was observed for a period of 2 minutes directly after undoing of litigation, as to exhibit a high level of haemostasis effect as indicated in FIG. 15. Meanwhile, when the cut-out surface 5 was untreated, 10 g or more bleeding was observed for same period and under same conditions.

A7. Tissue Antiadhesion

An experiment of tissue antiadhesion was made by the adhesive resin using the powder dextran aldehyde obtained in Section A1 and the neutral polylysine solution obtained in Section A2. An SD (Sprague-Dawley) rat having 300 g of body mass was subjected to midline incision; and then, left-hand-side peritoneum and a portion of muscle layers were removed in a square-shaped area having about 2.5 cm on each side, with a depth of about 1 mm. An electronic scalpel was applied to whole of the square-shaped area. Subsequently, 1 g of the powder-form first part of the adhesive was thinly and almost evenly sprayed on the square-shaped area by use of the hand-made device of Section A4; and thereon, 0.3 mL of the liquid-form second part of the adhesive was thinly and almost evenly applied by dropping. Further thereon, 1 g of the powder-form first part was sprayed by use of the hand-made device. Then, two minutes later, abdominal cavity was closed.

Figure 16:
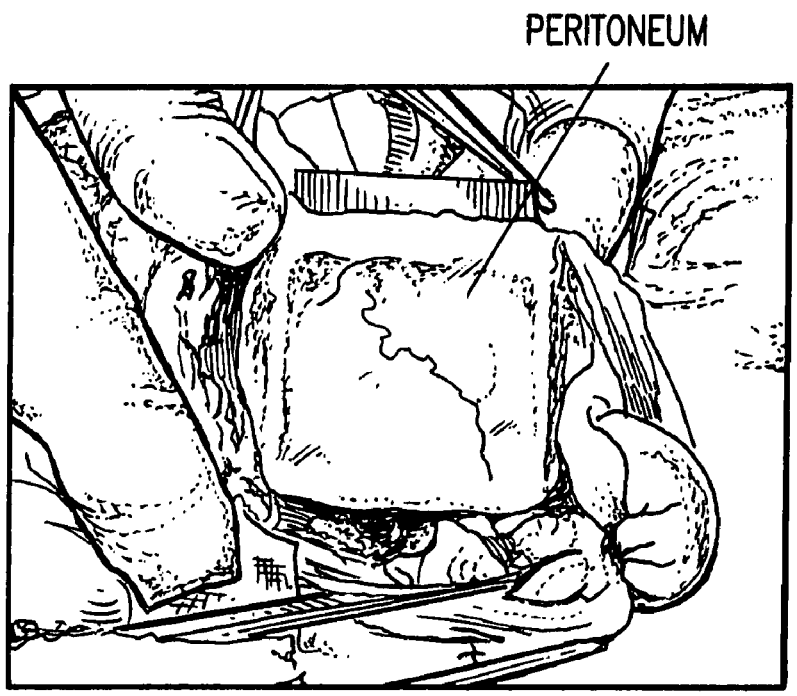
FIG. 16 is a photograph of cut-opened abdomen of a rat, showing that tissue adhesion has been curbed by the two-part adhesive of the embodiments.
Figure 17:
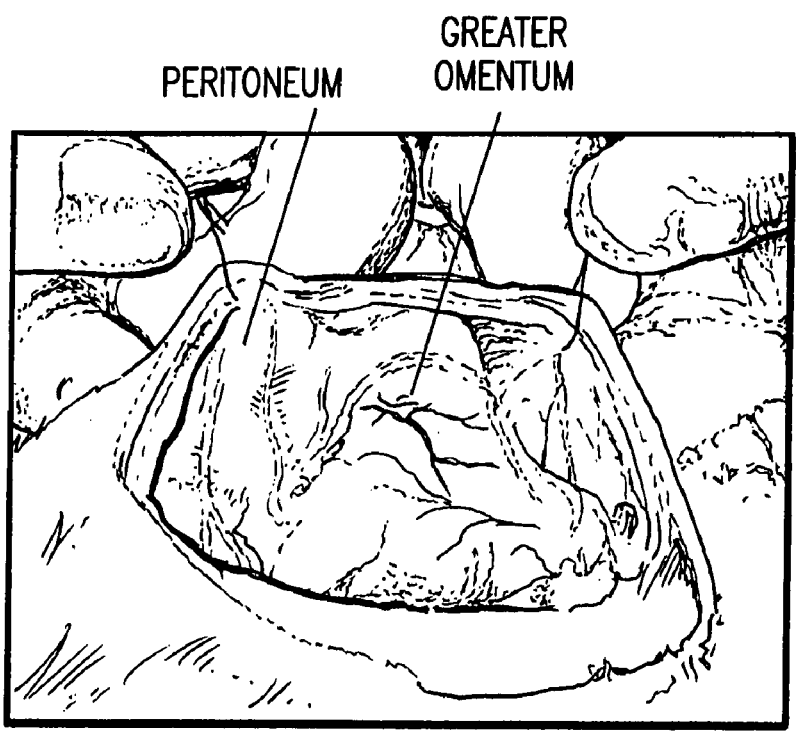
FIG. 17 is a photograph of cut-opened abdomen of a rat in a manner of FIG. 16, showing that tissue adhesion has been curbed by marketed Seprafilm.
Figure 18:
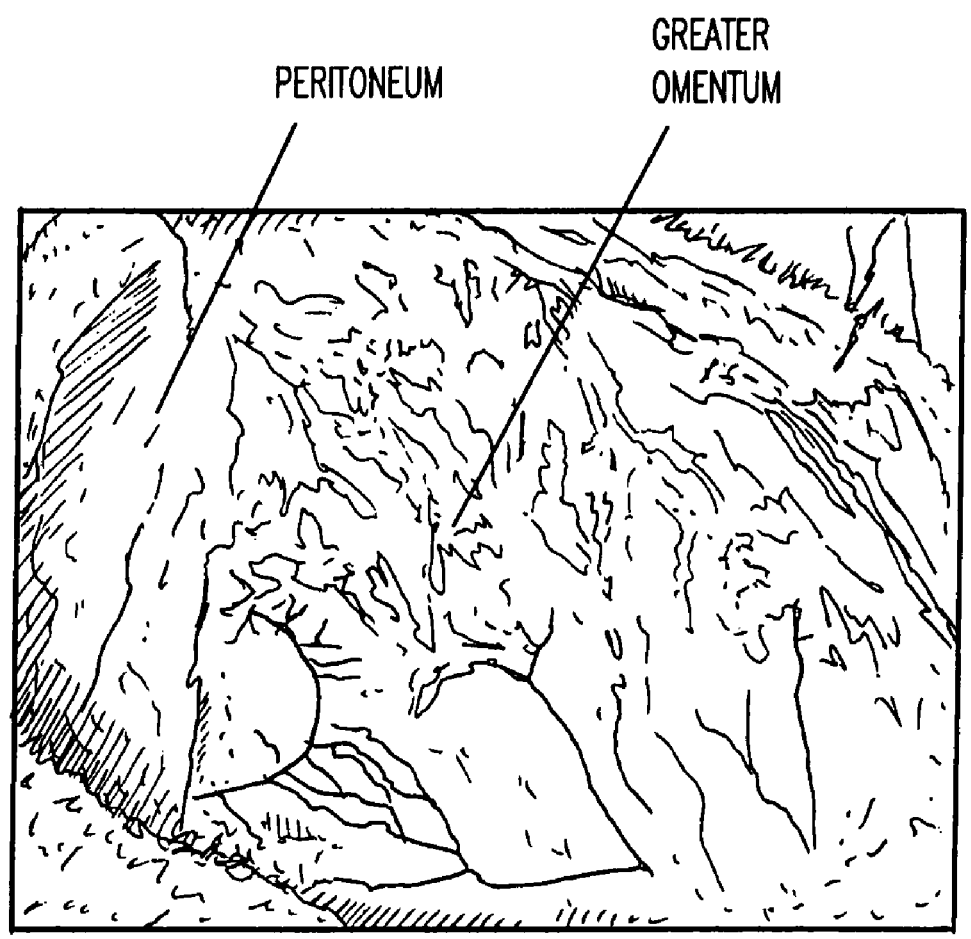
FIG. 18 is a photograph of cut-opened abdomen of a rat in a manner of FIG. 16, showing tissue adhesion when no adhesion barrier membrane was used.

Two weeks later, the abdominal cavity was opened and the extent of tissue adhesion between the peritoneum and a greater omentum was graded by a following three-grade scoring; "0" for no adhesion, "1" for peelable and mild adhesion and "2" for non-peelable and strong adhesion. For comparison, an adhesion barrier membrane (Seprafilm™ of Genzyme Corporation) having been on sale was attached on the square-shaped area on each of the rats in a comparison group. Obtained scoring of tissue adhesion was; 2.0±0.0 for a group of rats with no anti-adhesion membrane, 1.1±0.7 for "Seprafilm" group, and 0.4±0.5 for a group of rats treated with the adhesive mentioned on top of this section. Probabilities of non-existence of significant difference from the non-treatment group are as follows; P=0.02 for the "Seprafilm" group and P=0.0001 for the group of the adhesive of the embodiment. Number of samples in each group was; 6 for the non-treatment group, 9 for the "Seprafilm" group and 10 for the embodiment group. As clear from photographs of FIGS. 16-18, the seprafilm group (FIG. 17) and the embodiment group (FIG. 16) showed significant tissue anti-adhesion effect compared to the non-treatment group (FIG. 18); and the embodiment group (FIG. 16) showed a significantly higher tissue anti-adhesion effect than the Seprafilm group (FIG. 17), with probabilities of non-existence of significant difference being 0.03. As shown in an example of FIG. 16 for the embodiment, tissue adhesion between the peritoneum and the greater omentum was mild even when being existed. On contrary, example of FIG. 17 for the Seprafilm group showed a tissue adhesion in a large area.

TABLE 6

Tissue Anti-adhesion effect

| | Tissue adhesion extent | Non-significancy Probability from Non-treatment | Non-significancy Probability from Seprafilm |
|---|---|---|---|
| Non-treatment | 2.0 ± 0.0 | | |
| Seprafilm | 1.1 ± 0.7 | P = 0.02 | |
| Embodiment | 0.4 ± 0.5 | P = 0.0001 | P = 0.03 |

EMBODIMENTS OF THE THIRD ASPECT

Two-Powder Medical Adhesive

B1. Powder Dextran Aldehyde (the First Part) and Powder Polylysine (the Second Part)

"Dextran 70 powder J.P., Pharmaceutical grade (for injections)" of Meito Sangyo Co., Ltd. was used. Except for this, the powder dextran aldehyde was obtained in same manner as described in Section A1, and was used as the first part of the adhesive in following experiments. The amount of the introduced aldehyde groups per anhydroglucose unit (mole), which was measured in same manner as in Section 1, was 0.28 as same as in Section A1. Stereomicroscopic evaluation as same as in Section A1 revealed that; the powder has an average particle diameter of about 90 micrometer. Similarly, the powder was revealed to have porous nature.

Meanwhile, the neutral polylysine aqueous solution that had been used in Section 3 was dried to obtain a powder and was used as the second part of the adhesive. When the powder dextran aldehyde and the powder polylysine, in this Section B1, were mixed in weight ratio of 4/1, molar ratio of aldehyde groups and the amino groups becomes almost 1. In following experiments, used was such a powder mixture adhesive, in which the powder-form first and second parts of the adhesive are mixed with each other, with the molar ratio of almost 1.

B2. Use in Respiratory Surgery—Obturation of Air Leakage from Lung

Figure 19:
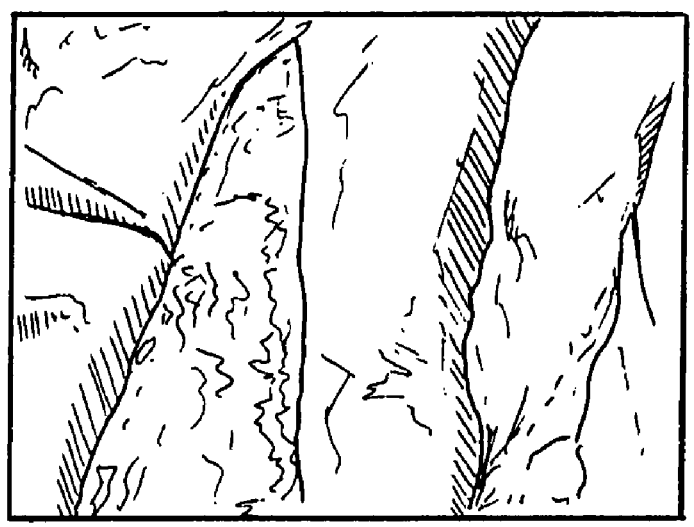
FIG. 19 is a photograph in a manner of FIG. 11-2, showing that air leakage through a pleural deficient area from a lung has been curbed by the two-powder adhesive.

To confirm obturation of the air leakage from lung, the experiment in same manner as described in Section 16 was made by use of a beagle dog; except that the pleural deficient area was formed in a circular area having diameter of 15 mm, which is a dark color part at near center of FIG. 19 and slightly leftwardly deviated from the center, and except that spreading of the adhesive was made as follows. Firstly, about 0.5 mL of physiologic saline was evenly dropped on the plural deficient area and its surroundings by use of 1 mL volume syringe. Thereon, 0.2 g of the powder mixture adhesive was almost evenly and thinly sprayed by use of the hand-made spray device (FIGS. 13-14) of Section 4. Further thereon, about 0.5 mL of physiological saline was again dropped. FIG. 19 is a photograph showing the pleural deficient area that is obturated by the above procedures. As seen from the FIG. 19, the obturation is achieved by hydrogel resin, as in same manner with FIG. 11-2.

Two minutes later, a pressure applied through the air way (respiratory tract) by an artificial respirator was increased gradually from 5 cmH$_2$O. Then, air leakage was observed at a pressure in a range of 35 to 50 cmH$_2$O. Thus, even by such a simple experiment, the adhesive of the embodiment was confirmed to effect obturation of air leakage at least in same level with the fibrin glue.

B3. Obliteration of a Pinhole on an Artificial Blood Vessel

An artificial blood vessel (Gore-Tex™, diameter of 8 mm) was perforated to have a pinhole of 18 G (outer diameter of 1.3 mm for circular area). Then, the powder mixture adhesive was sprayed to be applied there. In detail, on vicinity (area of 1 cm$^2$) of the pinhole, dropping of distilled water by the 1 mL syringe and applying of the powder mixture adhesive (aldehyde group/amino group molar ratio=1) by use of the hand-made spray device (FIGS. 13-14) were made as in following sequence; #1—dropping of distilled water, #2—spraying of the powder mixture adhesive, #3—dropping of distilled water, #4—spraying of the powder mixture adhesive, and #5—dropping of distilled water. Spread of the powder mixture adhesive as a sum of two times of application was about 0.2 g/cm$^2$. Two minutes later, hydraulic pressure was applied with water from one end of the blood vessel and effect of preventing of water leakage through the pinhole was evaluated. As a result of a rough estimate, the hydrogel resin layer withstood against up to about 200 mmHg of hydraulic pressure. This suggests that the two-powder medical adhesive may be applicable in cardiovascular surgery.

Such obliteration effect on the pinhole of the two-powder medical adhesive as a result of the rough estimate was same or more to that of the two-liquid medical adhesive of the Examples 1 and 2. For the rough estimate, applying of the two-liquid medical adhesive was made as follows; 2 mL of liquid mixture adhesive was dropped by use of the mixing device dedicated to mixing of reactive liquids; and then, the adhesive was spreaded by rubbing with fingers for 10 seconds. Two minutes later, the hydraulic pressure was applied as in same manner with the hydrogel layer formed by the two-powder medical adhesive.

B4. Degradability in Abdominal Cavity

A rat was anesthetized and subjected to midline incision; and then, right-hand-side peritoneum and a portion of muscle layers were removed in a square shape having about 2.5 cm on each side, with a depth of about 1 mm, to form a peritoneum deficient area. On the peritoneum deficient area, spraying of physiological saline by a spray bottle and applying of the applying of the powder mixture adhesive (aldehyde group/amino group molar ratio=1) by use of the hand-made spray device (FIGS. 13-14) were made as in following sequence; #1—dropping of physiological saline, #2—spraying of the powder mixture adhesive, #3—dropping of physiological saline, #4—spraying of the powder mixture adhesive, and #5—dropping of physiological saline. Spread of the powder mixture adhesive on each time of spraying was about 0.1 g/cm$^2$ so that total spread of the adhesive was about 0.2 g/cm$^2$; and spread of the physiological saline was 0.1 mL/cm$^2$ at each spraying.

Figure 20:
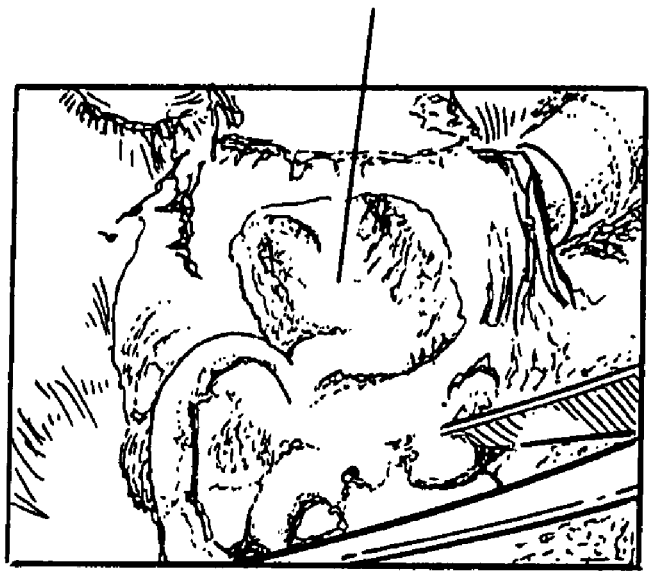
FIG. 20 is a photograph showing cut-opened abdomen of a rat, after a hydrogel layer of cured adhesive has been implanted and left there for a week.

One week later, the abdomen cavity was opened and remnant of the hydrogel resin layer of the adhesive was observed by naked eye, as to reveal that about 50% of the hydrogel resin layer was remained as shown in FIG. 20. In a photograph image of the FIG. 20, the hydrogel resin layer covers a circular exposed area, which is arranged at near center as slightly shifted upward from the center. When the two-liquid medical adhesive of the Example 1 on Section 7 was used in place of the adhesive of this section, about 90% or more of the hydrogel resin layer was disappeared on elapse of one week. Hence, disintegration rate of the two-powder medical adhesive was observed to be smaller than that of the two-liquid adhesive. Therefore, it was revealed that; the two-powder medical adhesive is applicable to an occasion requiring 1-2 weeks or more of retention period, such as haemostasis on liver, even without addition of polycarboxylic acids as in Section 8, and without addition of high-molecular-weight amine-groups containing polymer as in Section 6.

Haemostasis performance of the two-powder adhesive was revealed to be superior to the two-liquid adhesive of Examples 1 and 2, because the two-powder adhesive is more excellent in absorbing moisture in the tissues. Thus, the two-powder adhesive was observed to be capable of sufficiently arresting blood oozing or similar extent of bleeding.

B5. Haemostasis in Cutting Out Part of Kidney

Figures 1, 21:
Figures 2, 21:
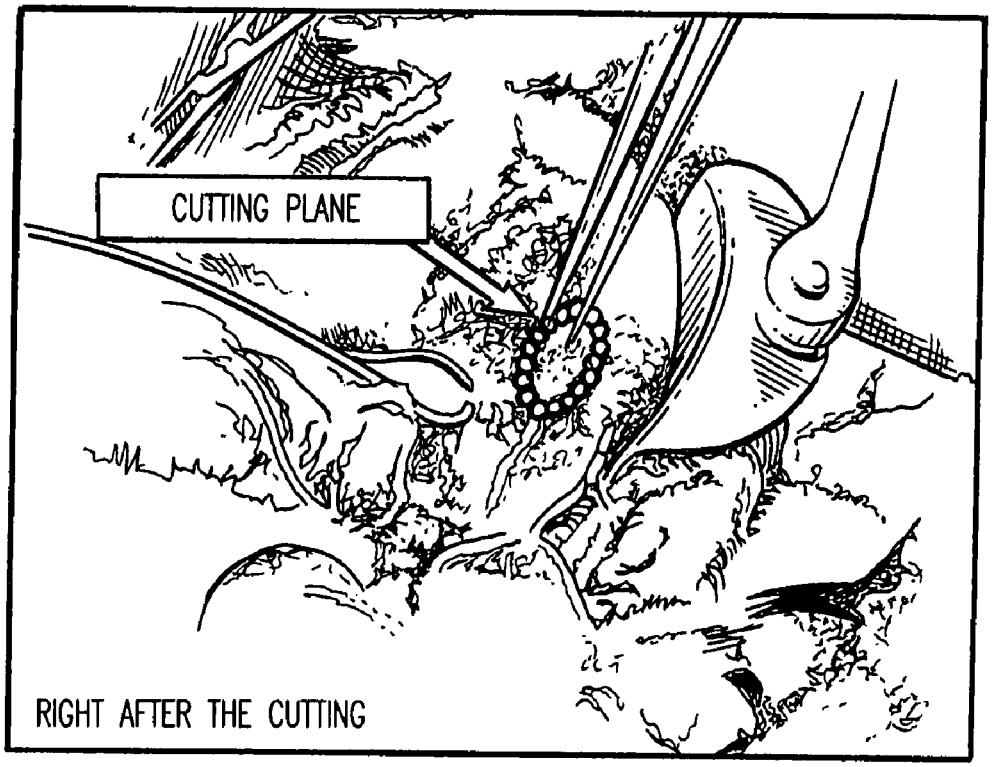
Figures 3, 21:

A rabbit was used to explore whether it is capable to arrest bleeding from a cut-out face that is formed by cutting out of a portion of the kidney. In same manner as in Section A6, in which the two-liquid adhesive was used in arresting of bleeding of liver, arteries in the kidney were clamped and partially cut out, and bleeding was arrested by the two-powder adhesive. FIGS. 21-1 to 21-3 are photographs showing these procedures; FIG. 21-1 shows the kidney to be cut out; FIG. 21-2 shows the kidney right after the cutting; and FIG. 21-3 shows the cut-out face having been applied with the adhesive. Application of the two-powder adhesive was made in same manner as in Section B2, as follows. On the cut-out face of about 5 cm$^2$ area, repeated twice were; dropping of 1 mL of physiological saline by 1 mL syringe and thereafter spraying of 0.5 g of the powder mixture adhesive. And, finally, 1 mL of physiological saline was dropped there. Two minutes later, the clamping was released and bleeding amount was evaluated by measuring weight of a gauze pad before and after absorbing of blood bled out from the cut-out face. Total amount of bleeding for 10 minutes period was measured as 0.3 g for a group treated with the two-powder adhesive and 20 g for a non-treated group. Thus, the two-powder medical adhesive of the embodiments is expected to have sufficient haemostasis performance when for partially cutting out of kidney.

Alpha-Glucan Aldehyde Sheet

Dextran aldehyde having 0.26 aldehyde groups per anhydroglucose unit (—CHO=0.264±0.003/sugar residue) was prepared from dextran (Wako Pure Chemical Industries, Ltd; Lot No. EWK3037) having weight-average molecular weight of 75,000, in a method described in Section 1 and Section A1. Then, 15 g of thus obtained dextran aldehyde was mixed with 3.75 g of glycerin and 131.25 mL of distilled water; and this mixture was kept at 50° C. and being agitated as to achieve a solution. The solution was poured as evenly spreaded for cast forming on a polyethylene sheet, which has thickness of 40 micrometers and had been pasted on a glass plate having dimensions of 20×20×0.5 cm. Subsequently, such a layer of cast solution was air dried at 25° C. for 24 hours, as to form a dextran aldehyde sheet having thickness of about 0.5 mm.

As explained by way of an experimental example below, the dextran aldehyde sheet may be used in combination of the two-part adhesive described in the above. In same manner with Section 16, following experiment was made by use of a beagle dog to confirm obturation of the air leakage from lung. In accordance with common procedures, conducted were anesthesia, endotracheal intubation, and then opening of thorax; and a pleural deficient area of 3×3 cm was cut out on right lung by use of an electrical scalpel. Physiological saline was sprayed on the deficient area, and pressure of respirator was increased, as to confirm occurrence of air leakage. Subsequently, by use of a mixing device dedicated to mixing of two-part liquids, about 2 mL of the adhesive of Reference Example 3 as in Section 16 was dropped on the deficient area. Immediately after the dropping of the adhesive, the dextran sheet that had been cut in a square shape having an area of 5×5 cm was pasted on the pleural deficient area. Two minutes later, thorax was filled with physiological saline and a leakage test was made. Resultantly, pressure at which air leakage was observed was 43.5±6.0 cmH$_2$O (sample number n=6, and standard deviation (SD)=6.0), which is significantly higher than the pressure of 33.3±4.8 cmH$_2$O, which has been obtained without using the dextran sheet.

The dextran aldehyde sheet having thickness in a range of 0.1 to 2 mm, preferably 0.3 to 0.8 mm may be used in combination with either of two-part adhesives and their usages explained in the above. Thus, the dextran aldehyde sheet may be used for leak stoppage, haemostasis, adhesion, tissue antiadhesion or the like, in combination with any of the two-liquid adhesives, the liquid-powder adhesives and the two-powder adhesives. In place of the dextran aldehyde sheet, a sheet of other alpha-glucan aldehyde such ad dextrin aldehyde may be used. Density of aldehyde groups per anhydroglucose unit is in a range of 0.1 to 1.0, preferably 0.2 to 0.9, still more preferably 0.3 to 0.8.

The invention claimed is:

1. Medical-use two-part adhesive comprising: a first part comprised of aldehyde-groups-introduced glucan having a weight-average molecular weight in a range of 1000 to 200,000 and a second part comprised of amino-groups-containing polymer that is at least one selected from a group consisting of epsilon-poly-L-lysine, alpha-poly-L-lysine, chitosan oligomer and degraded chitosan and has a molecular weight in a range of 1000 to 20,000; wherein
    the aldehyde-groups-introduced glucan is produced by oxidation of glucan with periodic acid or periodate, as to have aldehyde groups at a density of 0.1 to 1.0 per anhydroglucose unit; and
    a mixture of the first and second parts, which are aqueous solution and/or powder, at a time of mixing them or with water has pH in a range of 5.0 to 8.0.

2. Medical-use two-part adhesive according to claim 1, wherein the amino-groups-containing polymer is epsilon-poly-L-lysine produced by microorganism or by enzyme.

3. Medical-use two-part adhesive according to claim 1, wherein molar ratio of aldehyde groups to amino groups in the mixture of the first and second parts at a time of mixing them is in a range of 0.2 to 2.0.

4. Medical-use two-part adhesive according to claim 1, wherein the second part is added with: citric acid, succinic acid, glutar acid, malic acid, fumaric acid, maleic acid, or other polycarboxylic acid, or anhydride corresponding at least one of these acids; by 1 to 10 wt %.

5. Medical-use two-part adhesive according to claim 1 or 2, wherein the aldehyde-groups-introduced glucan is produced by oxidation of dextran having weight-average molecular weight in a range of 2000 to 100,000 or by oxidation of dextrin, with periodic acid or periodate, as to have aldehyde groups at a density of 0.2 to 0.9 per anhydroglucose unit.

6. Medical-use two-part adhesive according to claim 1 or 2, wherein the first and second parts have been subjected to sterilization with electron radiation in a range of 10 to 50KGy.

7. Medical-use two-part adhesive according to claim 1, wherein the first and second parts are aqueous solutions.

8. Medical-use two-part adhesive comprising: a first part comprised of powder of aldehyde-groups-introduced glucan having a weight-average molecular weight in a range of 1000 to 200,000 and a second part comprised of aqueous solution or powder of amino-groups-containing polymer that is formed of a polymer chain of amino-group-containing units and has a molecular weight in a range of 1000 to 20,000; wherein
    the aldehyde-groups-introduced glucan is produced by oxidation of glucan with periodic acid or periodate, as to have aldehyde groups at a density of 0.1 to 1.0 per anhydroglucose unit; and
    a mixture of the first and second parts at a time of mixing them has pH in a range of 5.0 to 8.0.

9. Medical-use two-part adhesive according to claim 8, wherein the amino-groups-containing polymer is epsilon-poly-L-lysine produced by microorganism or by enzyme.

10. Medical-use two-part adhesive according to claim 8, wherein molar ratio of aldehyde groups to amino groups in the mixture of the first and second parts at a time of mixing them is in a range of 0.2 to 4.0.

11. Medical-use two-part adhesive according to claim 8, wherein the second part is added with citric acid, succinic acid, glutaric acid, malic acid, fumaric acid, maleic acid, or other polycarboxylic acid, or anhydride corresponding at least one of these acids: by 1 to 10 wt %.

12. Medical-use two-part adhesive according to claim 8, wherein the aldehyde-groups-introduced glucan is produced by oxidation of dextran having weight-average molecular weight in a range of 2000 to 100,000 or by oxidation of dextrin, with periodic acid or periodate, as to have aldehyde groups at a density of 0.1 to 1.0 per anhydroglucose unit.

13. Medical-use two-part adhesive according to claim 8, wherein the first and second parts have been subjected to sterilization with electron radiation in a range of 10 to 50KGy.

14. Medical-use two-part adhesive according to claim 8, wherein the first and second parts are powders that are mixed with each other to form a powder mixture.

15. Medical-use two-part adhesive according to claim 14, wherein the powders are of a porous nature that is obtainable by freeze drying of aqueous solution and subsequent pulverization.

16. Medical-use two-part adhesive according to claim 8, wherein the second part is the aqueous solution.

17. Medical-use two-part adhesive comprising: a first part comprised of powder of aldehyde-groups-introduced glucan having a weight-average molecular weight in a range of 1000 to 200,000 and a second part comprised of powder of epsilon-poly-L-lysine that has a molecular weight in a range of 1000 to 20,000 and has been treated by adding with carboxylic anhydride; wherein
    the aldehyde-groups-introduced glucan is produced by oxidation of glucan with periodic acid or periodate, as to have aldehyde groups at a density of 0.1 to 1.0 per anhydroglucose unit;
    the medical-use two-part adhesive is in a form of a powder mixture formed of the first and second parts;
    molar ratio of aldehyde groups to amino groups in the powder mixture is about 1.0 to 3.5; and
    the powders are of a porous nature that is obtainable by freeze drying of aqueous solution and subsequent pulverization.

18. Medical-use two-part adhesive according to claim 17, wherein average particle diameter of the powders is around 90 micrometer.

19. Medical-use two-part adhesive according to claim 17, wherein the carboxylic anhydride is anhydride of: acetic acid, citric acid, succinic acid, glutaric acid, malic acid, fumaric acid, maleic acid, or other monocarboxylic acid or polycarboxylic acid.

20. Medical-use two-part adhesive according to claim 17, wherein the powder of the second part is obtained by dissolving the epsilon-poly-L-lysine having the molecular weight in a range of 1000 to 20,000 in water together with the carboxylic anhydride and subsequently by drying and pulverizing.

21. Medical-use two-part adhesive according to claim 17, wherein, when mixed with water, pH of an aqueous solution of the powder mixture is in a range of 5.0 to 8.0.

22. Medical-use two-part adhesive according to claim 17, wherein a portion of amino groups of the epsilon-poly-L-lysine is modified by the carboxylic anhydride.

23. Medical-use two-part adhesive comprising: a first part comprised of powder of aldehyde-groups-introduced glucan having a weight-average molecular weight in a range of 1000 to 200,000 and a second part comprised of powder of epsilon-poly-L-lysine that has a molecular weight in a range of 1000 to 20,000 and has been treated by adding with carboxylic acid; wherein
  the aldehyde-groups-introduced glucan is produced by oxidation of glucan with periodic acid or periodate, as to have aldehyde groups at a density of 0.1 to 1.0 per anhydroglucose unit;
  the medical-use two-part adhesive is in a form of a powder mixture formed of the first and second parts;
  molar ratio of aldehyde groups to amino groups in the powder mixture is about 1.0 to 3.5;
  the powders are of a porous nature that is obtainable by freeze drying of aqueous solution and subsequent pulverization; and
  the carboxylic acid is: acetic acid, citric acid, succinic acid, glutaric acid, malic acid, fumaric acid, maleic acid, or other monocarboxylic acid or polycarboxylic acid.

24. Medical-use resin in a form of hydrogel that is formed by mixing; a first part comprised of aldehyde-groups-introduced glucan having a weight-average molecular weight in a range of 1000 to 200,000; and a second part comprised of amino-groups-containing polymer that is at least one selected from a group consisting of epsilon-poly-L-lysine, alpha-poly-L-lysine, chitosan oligomer and degraded chitosan and has a molecular weight in a range of 1000 to 20,000; with molar ratio of aldehyde groups to amino groups in a range of 0.2 to 2.0; wherein
  the aldehyde-groups-introduced glucan is produced by oxidation of glucan with periodic acid or periodate, as to have aldehyde groups at a density of 0.1 to 1.0 per anhydroglucose unit; and
  said resin is fluidized at an elapse of gel-state preserving period that is able to be arbitrarily set in a range of one day to one month if said resin is kept in a form of hydrogel.

25. Medical-use kit for leak stoppage, haemostasis, adhesion or tissue antiadhesion, comprising:
  a first part comprised of powder of aldehyde-groups-introduced alpha-glucan having a weight-average molecular weight in a range of 1000 to 200,000;
  a second part comprised of aqueous solution or powder of amino-groups-containing polymer that is formed of a polymer chain of amino-group-containing units and has a molecular weight in a range of 1000 to 20,000; and
  a sheet of aldehyde-groups-introduced alpha-glucan having a weight-average molecular weight in a range of 1000 to 200,000;
  wherein
  the aldehyde-groups-introduced alpha-glucan is produced by oxidation of glucan with periodic acid or periodate, as to have aldehyde groups at a density of 0.1 to 1.0 per anhydroglucose unit; and
  a mixture of the first and second parts at a time of mixing them has pH in a range of 5.0 to 8.0 and thickness of the sheet is in a range of 0.1 to 10 mm in a dried state.

* * * * *